(12) United States Patent
Yallop

(10) Patent No.: US 7,608,431 B2
(45) Date of Patent: Oct. 27, 2009

(54) FED-BATCH PROCESS FOR PRODUCTION OF ERYTHROPOIETIN IN HUMAN EMBRYONIC RETINA CELLS THAT EXPRESS ADENOVIRUS E1A

(75) Inventor: Christopher A. Yallop, Wassenaar (NL)

(73) Assignee: Crucell Holland B.V., Leiden (NL)

( * ) Notice: Subject to any disclaimer, the term of this patent is extended or adjusted under 35 U.S.C. 154(b) by 282 days.

(21) Appl. No.: 11/331,861

(22) Filed: Jan. 13, 2006

(65) Prior Publication Data

US 2006/0121611 A1    Jun. 8, 2006

Related U.S. Application Data

(63) Continuation-in-part of application No. 11/259,245, filed on Oct. 26, 2005, which is a continuation of application No. PCT/EP2004/050724, filed on May 6, 2004.

(30) Foreign Application Priority Data

| May 9, 2003 | (WO) | ............... PCT/EP03/50155 |
| Sep. 1, 2003 | (WO) | ............... PCT/EP03/50390 |
| Dec. 4, 2003 | (WO) | ............... PCT/EP03/50940 |
| Jan. 30, 2004 | (WO) | ............ PCT/EP2004/050061 |

(51) Int. Cl.
- *C12P 21/04* (2006.01)
- *C12N 15/85* (2006.01)
- *C12N 15/09* (2006.01)
- *C12N 15/63* (2006.01)

(52) U.S. Cl. ............... 435/70.3; 435/325; 435/455
(58) Field of Classification Search ............... None
See application file for complete search history.

(56) References Cited

U.S. PATENT DOCUMENTS

| 4,703,008 | A | 10/1987 | Lin |
| 4,835,260 | A | 5/1989 | Shoemaker |
| 5,047,335 | A | 9/1991 | Paulson et al. |
| 5,192,539 | A | 3/1993 | Van Der Marel et al. |
| 5,441,868 | A | 8/1995 | Lin |
| 5,457,089 | A | 10/1995 | Fibi et al. |
| 5,494,790 | A | 2/1996 | Sasaki et al. |
| 5,767,078 | A | 6/1998 | Johnson et al. |
| 5,773,569 | A | 6/1998 | Wrighton et al. |
| 5,789,247 | A | 8/1998 | Ballay et al. |
| 5,830,851 | A | 11/1998 | Wrighton et al. |
| 5,835,382 | A | 11/1998 | Wilson et al. |
| 5,856,292 | A | 1/1999 | Thomas et al. |
| 5,856,298 | A | 1/1999 | Strickland |
| 5,994,128 | A | 11/1999 | Fallaux et al. |
| 6,033,908 | A | 3/2000 | Bout et al. |
| 6,395,519 | B1 | 5/2002 | Fallaux et al. |
| 6,413,746 | B1 | 7/2002 | Field |
| 6,492,169 | B1 | 12/2002 | Vogels et al. |
| 6,506,598 | B1 | 1/2003 | Andersen et al. |
| 6,558,948 | B1 | 5/2003 | Kochanek et al. |
| 6,653,101 | B1 | 11/2003 | Cockett et al. |
| 6,855,544 | B1 | 2/2005 | Hateboer et al. |
| 6,878,549 | B1 | 4/2005 | Vogels et al. |
| 7,132,280 | B2 * | 11/2006 | Bout et al. .................. 435/326 |
| 2002/0116723 | A1 | 8/2002 | Grigliatti et al. |
| 2003/0087437 | A1 | 5/2003 | Asada et al. |
| 2003/0092160 | A1 | 5/2003 | Bout et al. |
| 2005/0164386 | A1 | 7/2005 | Uytdehaag et al. |
| 2005/0181359 | A1 * | 8/2005 | Optelten et al. ................. 435/5 |
| 2005/0288220 | A1 | 12/2005 | Burg et al. |

FOREIGN PATENT DOCUMENTS

| EP | 0 185 573 | 6/1986 |
| EP | 0 411 678 | 2/1991 |
| EP | 0 833 934 B1 | 4/1998 |
| EP | 1 108 787 A2 | 6/2001 |
| WO | WO 93/03163 | 2/1993 |
| WO | WO 95/05465 | 2/1995 |
| WO | WO 95/29994 | 11/1995 |
| WO | WO 97/00326 | 1/1997 |
| WO | WO 97/18318 | 5/1997 |
| WO | WO 98/18926 | 5/1998 |
| WO | WO 98/39411 | 9/1998 |
| WO | WO 98/44141 | 10/1998 |
| WO | WO 99/05268 | 2/1999 |
| WO | WO 99/24068 | 5/1999 |
| WO | WO 00/61164 | 10/2000 |
| WO | WO 00/63403 A | 10/2000 |
| WO | WO 01/05945 A2 | 1/2001 |
| WO | WO 01/38362 A2 | 5/2001 |
| WO | WO 02/18948 | 3/2002 |

(Continued)

OTHER PUBLICATIONS

Kurokawa et al Biotech. Bioeng. 1994. vol. 44, pp. 95-103.*

(Continued)

Primary Examiner—Nancy Vogel
Assistant Examiner—Michele K. Joike
(74) Attorney, Agent, or Firm—TraskBritt

(57) ABSTRACT

The invention provides processes for recombinant production of erythropoietin (EPO) in a human embryonic retina cell that expresses at least an adenoviral E1A protein, wherein said EPO is produced at high concentrations and wherein said EPO as produced has a high average sialic acid content per EPO molecule.

19 Claims, 5 Drawing Sheets

FOREIGN PATENT DOCUMENTS

| WO | WO 02/053580 | | 7/2002 |
|---|---|---|---|
| WO | WO 03/003810 | A1 | 5/2003 |
| WO | WO 03/048197 | A1 | 6/2003 |
| WO | WO 03/048348 | A2 | 6/2003 |
| WO | WO 03/051927 | | 6/2003 |
| WO | WO 2004/003176 | | 1/2004 |
| WO | WO 2004058944 | A2 * | 7/2004 |
| WO | WO 2004/099396 | A1 | 11/2004 |
| WO | WO 2004099396 | A1 * | 11/2004 |

OTHER PUBLICATIONS www.peptideguide.com.*

Alkhatib et al., "Expression of Bicistronic Measles Virus P/C mRNA by Using Hybrid Adenovirus: Levels of C Protein Synthesized in Vivo Are Unaffected by the Presence or Absence of the Upstream P Initiator Codon," Journal of Virology, Nov. 1988, pp. 4059-4068, vol. 62, No. 11.

Alkhatib et al., "High-Level Eurcaryotic In Vivo Expression of Biologically Active Measles Virus Hemagglutinin by Using an Adenovirus Type 5 Helper-Free Vector System," Journal of Virology, Aug. 1988, pp. 2718-2727, vol. 62, No. 8.

Berg et al., High-Level Expression of Secreted Proteins from Cells Adapted to Serum-Free Suspension Culture, Research Report, BioTechniques 1993, pp. 972-978, vol. 14, No. 6.

Bout et al., "Improved helper cells for RCA-free production of E1-deleted recombinant adenovirus vectors," Cancer Gene Therapy, 1996, pp. S24, vol. 3, No. 6.

Bout et al., "PER.C6 as production platform for human monoclonal antibodies," Human Antibodies, Oct. 8, 2003, pp. 30, vol. 12, No. 1-2.

Bout et al., "Production of RCA-free batches of E1-deleted recombinant adenoviral vectors on PER.C6," Nucleic Acids Symp. Ser. 1998, XP-002115716, pp. 35-36.

Boutl et al., A novel packaging cell line (PER.C6) for efficient production of RCA-free batches of E1-deleted recombinant adenoviral vectors, Cancer Gene Therapy, 1997, pp. S32-S33, vol. 4, No. 6.

Brown et al., "Evaluation of Cell Line 293 for Virus isolation in Routine Viral Diagnosis," Journal of Clinical Microbiology, Apr. 1986, pp. 704-708, vol. 23, No. 4.

Bukreyev et al., "Recombinant Respiratory Syncytial Virus from Which the Entire SH Gene Has Been Deleted Grows Efficiently in Cell Culture and Exhibits Site-Specific Attenuation in the Respiratory Tract of the Mouse," Journal of Virology, Dec. 1997, pp. 8973-8982, vol. 71, No. 12.

Caravokyri et al., "Constitutive Episomal Expression of Polypeptide IX (pIX) in a 293-Based Cell Line Complements that Deficiency of pIX Mutant Adenovirus Type 5," Journal of Virology, Nov. 1995, pp. 6627-6633, vol. 69, No. 11.

Carroll et al., Abstract, Differential Infection of Receptor-modified Host Cells by Receptor-Specific Influenza Viruses, Virus Research, Sep. 1985, pp. 165-179, vol. 3, No. 2.

Certificate of deposit of the PER.C6 cell line (ECACC deposit under No. 96022940).

Ciccarone at al., "Lipofectamine 2000 Reagent for Transfection of Eukaryotic Cells," Focus, 1999, pp. 54-55, vol. 21, No. 2.

Cote et al., Serum-Free Production of Recombinant Proteins and Adenoviral Vectors by 293SF-3F6 Cells, Biotechnology and Bioengineering, Sep. 5, 1998, pp. 567-575, vol. 59, No. 5.

Cronan, Abstract, Biotination of Proteins in-vivo a post-translational modification to label purify and study proteins, Journal of Biological Chemistry, Jun. 25, 1990, pp. 10327-10333, vol. 265, No. 18.

DuBridge et al., "Analysis of Mutation in Human Cells by Using an Epstein-Barr Virus Shuttle System," Molecular and Cellular Biology, Jan. 1987, pp. 397-387, vol. 7, No. 1.

Endo et al., Growth of Influenza A Virus in Primary, Differentiated Epithelial Cells Derived from Adenoids, Journal of Virology, Mar. 1996, pp. 2055-2058, vol. 70, No. 3.

Fallaux et al, "New helper cells and matched early region 1-deleted adenovirus vectors prevent generation of replication-competent adenoviruses," Human Gene Therapy, Sep. 1, 1998, vol. 9, No. 1, pp. 1909-1917. Abstract.

Fallaux et al., Characterization of 911: A New Helper Cell Line for the Titration and Propagation of Early Region 1-Deleted Adenoviral Vectors, Human Gene Therapy, Jan. 20, 1996, pp. 215-222, vol. 7.

Gallimore et al., Transformation of Human Embryo Retinoblasts with Simian Virus 40, Adenovirus and ras Oncogenes, Anticancer Research, 1986, pp. 499-508, vol. 6.

Garnier et al., Scale-up of the adenovirus expression system for the production of recombinant protein in human 293S cells, Cytotechnology, 1994, pp. 145-155, vol. 15.

GenBank Accession No. X02996.1, 1993, "Adenovirus type 5 left 32% of the genome."

Ghosh-Choudhury et al., Protein IX, a minor component of the human adenovirus capsid, is essential for the packaging of the full length genomes, The EMBO Journal, 1987, pp. 1733-1739, vol. 6, No. 6.

GIBCO cell culture, A Guide to Serum-Free Cell Culture, www.invitrogen.com.

Grabenhorst et al., Construction of stable BHK-21 cells coexpressing human secretory glycoproteins and human Gal(beta-1-4)GlcNAc-R alpha-2,6-sialyltransferase alpha-2,6-Linked NeuAc is preferentially attached to the Gal(beta-1-4)GlcNAc(beta-1-2)Man(alpha-1-3)-branch of diantennary oligosaccharides from secreted recombinant beta-trace protein, Eur. J. Biochem, 1995, pp. 718-725, vol. 232, No. 3, Berlin, Germany.

Graham et al., "Characteristics of a Human Cell Line Transformed by DNA from Human Adenovirus Type 5," J. Gen. Virol., 1997, pp. 59-72, vol. 36.

Graham et al., "Growth of 293 cells in suspension culture," J Gen Virol, Mar. 1987, pp. 937-940, vol. 68.

Graham, Cell Lines, Promochem (visited Apr. 10, 2005) <http://www.lgcpromochem-atcc.com/SearchCatalogs/longview.cfm?view=ce,1146678 . . . >.

Grand et al., "Modulation of the level of expression of cellular genes in adenovirus 12-infected and transformed human cells," Eur Mol Biol Organ J. 1986, 5 (6) 1253-1260. Abstract.

Grand et al., "The high levels of p53 present in adenovirus early region 1-transformed human cells do not cause up-regulation of MDM2 expression," Virology, 1995, vol. 210, No. 2, pp. 323-334. Abstract.

Hollister et al., Stable expression of mammalian beta1,4-galactosyltransferase extends the N-glycosylation pathway in insect cells, Glycobiology, 1998, pp. 473-480, vol. 8, No. 5, IRL Press, United Kingdom.

Holzer et al., "Construction of a Vaccinia Virus Deficient in the Essential DNA Repair Enzyme Uracil DNA Glycosylase by a Complementing Cell Line," Journal of Virology, Jul. 1997, pp. 4997-5002, vol. 71, No. 7.

Inoue et al., Production of Recombinant Human Monoclonal Antibody Using ras-Amplified BHK-21 Cells in a Protein-free Medium, Biosci. Biotech. Biochem., 1996, pp. 811-817, vol. 60, No. 5.

Interlocutory Decision of the Opposition Division of Jul. 21, 2003 in the case EP 0 695 351(European application 94 913 174.2).

Jenkins et al., Getting the glycosylation right: Implications for the biotechnology industry, Nature Biotechnology, Aug. 1996, pp. 975-981, vol. 14, No. 8, Nature Publishing, US.

Jones et al., "High-Level Expression of Recombinant IgG in the Human Cell Line PER.C6," Biotechnology Progress, Jan. 14, 2003, pp. 163-168, vol. 19.

Jones et al., "PER.C6 Cell LIne for Human Antibody Production: Crucell's Technology Maintains ' Human' Glycoylation Patterns," Genetic Engineering News, May 15, 2002, pp. 50, 54, vol. 80, No. 5.

Lopez et al., Efficient production of biologically active human recombinant proteins in human lymphoblastoid cells form integrative and episomal expression vectors, Gene, 1994, pp. 285-291, vol. 148.

Louis et al., Cloning and Sequencing of the Cellular-Viral Junctions from the Human Adenovirus Type 5 Transformed 293 Cell Line, Virology, 1997, pp. 423-429, vol. 233.

Lutz et al., "The Product of the Adenovirus Intermediate Gene IX Is a Transcriptional Activator," Journal of Virology, Jul. 1997, pp. 5102-5109, vol. 71, No. 7.

Manservigi et al., "Protection from Herpes Simplex Virus Type 1 Lethal and Latent Infections by Secreted Recombinant Glycoprotein B Constitutively Expressed in Human Cells with a BK Virus Episomal Vector," Journal of Virology, Jan. 1990, pp. 431-436, vol. 64, No. 1.

Massie et al., Improved Adenovirus Vector Provides Herpes Simplex Virus Ribonucleotide Reductase R1 and R2 Subunits Very Efficiently, Biotechnology, Jun. 1995, pp. 602-608, vol. 13.

Merten at al., Production of Influenza Virus in Cell Cultures for Vaccine Preparation, Exp Med Biol., 1996, pp. 141-151, vol. 397.

Minch et al., Tissue Plasminogen Activator Coexpressed in Chinese Hamster Ovary Cells with alpha(2,6)-Sialyltransferase Contains NeuAc-alpha(2,6)Gal-beta(1,4)Glc-N-AcR Linkages, Biotechnol. Prog., 1995, pp. 348-351, vol. 11, No. 3.

NCBI Entrez Nucleotide accession No. NC_002018.

NCBI Entrez Nucleotide accession No. U38242.

NCBI Entrez Nucleotide accession No. X02996 J01967 J01968 J01970 J01971 J01972 J01974 J01976 J01977 J01978 J01979 K00515 V00025 V00026 V00027 V00029.

Neumann et al., "Generation of influenza A viruses entirely from cloned cDNAs," Proc. Natl. Acad. Sci., Aug. 1999, pp. 9345-9350, vol. 96.

Notice of Opposition to a European Patent for 1 161 548 by Serono.

Opposition against European patent 1 108 878 B1 filed Oct. 5, 2005 in the name and on behalf of CEVEC Pharmaceuticals GmbH.

Opposition against European patent 1 161 548 B1 filed Nov. 16, 2005, in the name and on behalf of CEVEC Pharmaceutical GmbH.

Opposition against European patent 1108787 filed Oct. 5, 2005 in the name and on behalf of Probiogen AG.

Ory et al., "A stable human-derived packaging cell line for production of high titer retrovirus/vesicular stomatitis virus G pseudotypes," Proc. Natl. Acad. Sci., Oct. 1996, pp. 11400-11406, vol. 93.

Pacitti et al., Inhibition of Reovirus Type 3 Binding to Host Cells by Sialylated Glycoproteins Is Mediated through the Viral Attachment Protein, Journal of Virology, May 1987, pp. 1407-1415, vol. 61, No. 5, American Society for Microbiology.

Parkinson et al., "Stable Expression of a Secretable Deletion Mutant of Recombinant Human Thrombomodulin in Mammalian Cells," The Journal of Biological Chemistry, Jul. 25, 1990, pp. 12602-12610, vol. 265, No. 21.

Pau at al., Abstract, The human cell line PER.C6 provides a new manufacturing system for the production of influenza vaccines, Vaccine, Mar. 21, 2001, pp. 2716-2721, vol. 19, No. 17-19.

Paul et al., Increased Viral Titer Through Concentration of Viral Harvests from Retroviral Packaging Lines, Human Gene Therapy, 1993, pp. 609-615, vol. 4.

Pazur at al., Abstract, Oligosaccharides as immunodeterminants of erythropoietin for two sets of anti-carbohydrate antibodies, Journal of Protein Chemistry, Nov. 2000, pp. 631-635, vol. 19, No. 8.

Pham et al., "Large-Scale Transient Transfection of Serum-Free Suspension-Growing HEK293 EBNA1 Cells: Peptone Additives Improve Cell Growth and Transfection Efficieny," Biotechnology and Bioengineering, Nov. 5, 2003, pp. 332-342, vol. 84, No. 3.

Pleschka at al., "A Plasmid-Based Reverse Genetics System for Influenza A Virus," Journal of Virology, Jun. 1996, pp. 4188-4192, vol. 70, No. 6.

PubMed listing of abstracts (visited Apr. 10, 2005) <http://www.ncbi.nlm.nih.gov/entrez/query.fcgi?CMD=search&DB=pubmed.

Reina at al., Comparison of Madin-Darby Canine Kidney cells (MDCK) with a Green Monkey Continuous Cell Line (Vero) and Human Lung Embryonated Cells (MRC-5) in the Isolation of Influenza A Virus from Nasopharyngeal Aspirates by Shell Vial Culture, Journal of Clinical Microbiology, Jul. 1997, pp. 1900-1901, vol. 35, No. 7.

Rhim et al., "Development of Human Cell Lines from Multiple Organs," Annals of the New York Academy of Sciences, 2000, pp. 16-25, vol. 919.

Schiedner et al., Abstract, Efficient transformation of primary human amniocytes by E1 functions of Ad5: generation of new cell lines for adenoviral vector production, 2000, Hum. Gene Ther. 11, 2105-2116.

Setoguchi et al., "Stimulation of Erythropoiesis by in vivo gene therapy: Physiologic consequences of transfer of the humanerythropoietin gene to experimental animals using an adenovirus vector," Blood, Nov. 1, 1994, pp. 2946-2953, vol. 84, No. 9.

Spector et al., "Regulation of Integrated Adenovirus Sequences During Adenovirus Infection of Transformed Cells," Journal of Virology, Dec. 1980, pp. 860-871, vol. 36, No. 3.

Stevens et al., "The N-Terminal Extension of the Influenza B Virus Nucleoprotein Is Not Required for Nuclear Accumulation or the Expression and Replication of a Model RNA," Journal of Virology, Jun. 1998, pp. 5307-5312, vol. 72, No. 6.

Stockwell et al., High-throughput screening of small molecules in Miniaturized Mammalian Cell-based Assays involving Post-translational Modifications, Chemistry and Biology, Feb. 1999, pp. 71-83, vol. 6, No. 2.

U.S. Department of Health and Human Services, Public Health Service, Food and drug Administration, Center for Biologics Evaluation and Research, International Association for Biologicals, National Institute of Allergy and Infectious Diseases, National Vaccine Program Office, World Health Organization, Evolving Scientific and Regulatory Perspectives on Cell Substrates for Vaccine Development, Workshop, Friday, Sep. 10, 1999 (visited Sep. 30, 2005) <http://www.fda.gov.cber.minutes/0910evolv.txt>.

Weikert et al., Engineering Chinese hamster ovary cells to maximize sialic acid content of recombinant glycoproteins, Nature Biotechnology, Nov. 1999, pp. 1116-1121, vol. 17, No. 11, Nature Pub. Co., New York, NY, US.

Xie et al., "Large-Scale Propagation of a Replication-Defective Adenovirus Vector in Stirred-Tank Bioreactor PER.C6 Cell Culture Under Sparging Conditions," Jul. 5, 2003, Biotechnology and Bioengineering, pp. 45-52, vol. 83, No. 1.

Xie et al., "Serum-Free Suspension Cultivation of PER.C6 Cells and Recombinant Adenovirus Production Under Different pH Conditions," Biotechnology and Bioengineering, Dec. 5, 2002, pp. 569-579, vol. 80, No. 5.

Yan et al., Novel Asn-linked oligosaccharides terminating in GalNAcbeta(1-4)[Fucalpha(1-3)]GlcNAcbeta(1-.) are present in recombinant human Protein C expressed in human kidney 293 cells, Glycobiology, 1993, pp. 597-608, vol. 3. No. 6.

Yeager et al., Constructing immortalized human cell lines, Current Opinion Biotechnology, 1999, pp. 465-469, vol. 10.

Yeh et al., Adenoviral Vectors, pp. 25-42 of "Concepts in Gene Therapy," Publisher: Walter de Gruyter, New York.

Yu et al., "Enhanced c-erbB-2/neu expression in human ovarian cancer cells correlates with more severe malignancy that can be suppressed by E1A," Cancer Res., 1993, 53 (4) 891-8. Abstract.

Zhang et al., Stable expression of human alpha-2,6-sialyltransferase in Chinese hamster ovary cells: functional consequences for human erythropoietin expression and bioactivity, BBA—General Subjects, 1998, pp. 441-452, vol. 1425, No. 3, Elsevier Science Publishers, NL.

U.S. Appl. No. 11/544,490, filed Oct. 9, 2006, Christopher A. Yallop, Cultures of E1-Immortalized Cells and Processes for Culturing the Same to Increase Product Yields Therefrom.

* cited by examiner

Average EPO Yield

Clone

FED-BATCH PROCESS FOR PRODUCTION OF ERYTHROPOIETIN IN HUMAN EMBRYONIC RETINA CELLS THAT EXPRESS ADENOVIRUS E1A

CROSS-REFERENCE TO RELATED APPLICATIONS

This application is a continuation-in-part of U.S. patent application Ser. No. 11/259,245, filed Oct. 26, 2005, which itself is a continuation of International Patent Application PCT/EP2004/050724, filed May 6, 2004, designating the United States of America, published, in English, as International Patent Publication WO 2004/099396 A1 on Nov. 18, 2004, which itself claims priority from International Patent Application Nos. PCT/EP03/50155 filed May 9, 2003, PCT/EP03/50390 filed Sep. 1, 2003, PCT/EP03/50940 filed Dec. 4, 2003, and PCT/EP04/050061 filed Jan. 30, 2004, the contents of the entirety of each of which are incorporated by this reference.

FIELD OF THE INVENTION

The invention relates generally biotechnology in area of cell culture. In particular, the invention relates to the field of culturing cells derived from cells that have been immortalized with E1 sequences from adenovirus. More in particular, the invention relates to culturing such cells to obtain high levels of products from such cells.

BACKGROUND OF THE INVENTION

A human PER.C6 cell line, exemplified by cells deposited at the ECACC under No. 96022940, derived from retina cells by immortalization with the adenovirus (Ad5) E1a and E1b genes is disclosed in U.S. Pat. No. 5,994,128. Besides the ability to function as packaging cells for E1-deleted adenoviral vectors (U.S. Pat. No. 5,994,128; WO 01/005945), and for producing other viruses (WO 01/38362), E1-immortalized cells, such as PER.C6 cells, can be used to produce recombinant proteins, such as antibodies (WO 00/63403).

Xie et al. (2002) have disclosed a process for serum-free suspension cultivation of E1-immortalized cells. However, the product yields obtained using the culturing processes disclosed in the art for E1-immortalized cells, can be improved.

SUMMARY OF THE INVENTION

In particular embodiments, the present invention provides processes to increase the product yield from E1-immortalized cells.

In certain embodiments, the invention provides feed strategies for fed-batch or fed-perfusion cultures of cells immortalized by adenovirus E1 sequences. In one embodiment thereof, the invention provides a method for the culturing of such cells, the cells capable of growing in suspension, comprising the steps of: determining at least once during the culturing of the cells the concentration of at least one medium component selected from the group consisting of glucose, glutamine phosphate, leucine, serine, isoleucine, arginine, methionine, cystine, valine, lysine, threonine and glycine, adding components to the medium during the culturing of the cells at or prior to the depletion of at least one of the components of which the concentration was determined in the previous step, wherein the components added at least comprise glucose, glutamine, phosphate, leucine, serine, isoleucine, arginine, methionine, and cystine. Other components that beneficially may be added according to the invention, amounts and time of addition of the components are provided herein below, as well as in the claims.

In another embodiment, the invention provides a culture of cells derived from cells immortalized by adenovirus E1 sequences, characterized in that the culture comprises at least $10 \times 10^6$ cells/ml. Preferably, the culture comprises at least $12 \times 10^6$ cells/ml, more preferably, at least $15 \times 10^6$ cells/ml. In certain preferred embodiments, the culture according to the invention comprises more than $20 \times 10^6$, $25 \times 10^6$, $30 \times 10^6$ or $40 \times 10^6$ cells/ml. Methods to obtain such cultures are also provided herein.

In yet another aspect, a method to increase cell densities and product yields from a culture of cells immortalized by adenovirus E1 sequences is provided. In one embodiment hereof, a process for culturing such cells is provided, characterized in that the process comprises a step of subculturing the cells at a seeding concentration of between $0.8 \times 10^6$ and $2.0 \times 10^6$ viable cells/ml, preferably, between $0.9 \times 10^6$ and $1.5 \times 10^6$ viable cells/ml.

Preferably, the cells used in the methods of the invention are derived from retina cells, more preferably, from human embryonic retina (HER) cells, such the cells deposited under ECACC No. 96022940. In certain embodiments, the cells are PER.C6 cells.

In certain embodiments, the cells can produce recombinant proteins, preferably, antibodies, at high yields. In other embodiments, the cells comprise recombinant adenoviral vectors having a deletion in the E1-region, or other viruses, which can be produced on the cells in high yields using the process according to the invention. In preferred embodiments, the cells are cultured at least part of the time in a serum-free medium.

The present invention further provides processes to produce erythropoietin (EPO) with high yields and having a high sialic acid content. In particular, the present invention provides a process for recombinant production of erythropoietin (EPO) in a human embryonic retina cell that expresses at least an adenoviral E1A protein, wherein said EPO is produced at a concentration of at least 3000 eU/ml, and wherein said EPO as produced has an average sialic acid content per EPO molecule of at least 7, preferably at least 8, the process comprising: a) providing an immortalized human embryonic retina cell that expresses at least an adenoviral E1A protein, said cell further comprising a nucleic acid encoding a sialyltransferase under control of a heterologous promoter, and said cell further comprising nucleic acid encoding EPO under control of a heterologous promoter; b) culturing the cell in a serum-free culture medium in a fed-batch process, wherein at least once during said culturing according to needs of nutrients at least one essential amino acid and at least one carbohydrate are added depending on the requirements of the cells; and c) harvesting EPO from the culture medium, wherein the EPO is present in the culture medium at a concentration of at least 3000 eU/ml and wherein said EPO as produced has an average sialic acid content per EPO molecule of at least 7, preferably at least 8.

DETAILED DESCRIPTION OF THE INVENTION

Figure 1:
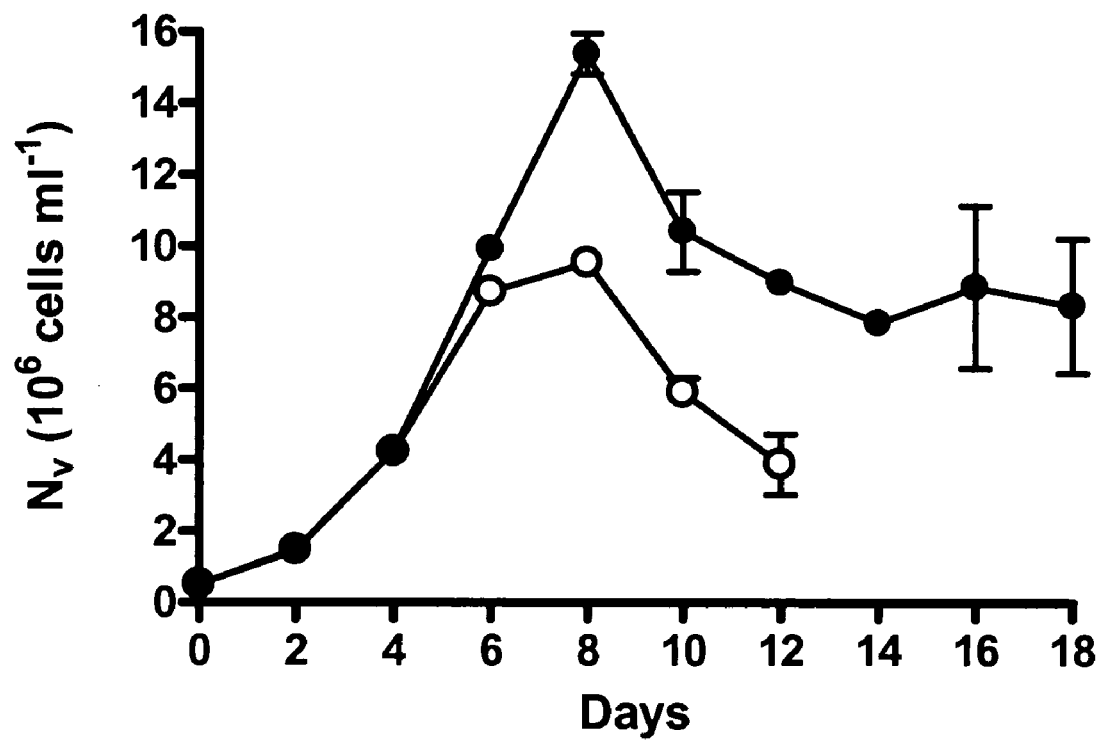
FIG. 1. Viable cell numbers ($N_v$) and antibody (Ab) concentration obtained in a batch (open circles) and a fed-batch (closed circles) process for antibody expressing clone 4a. See example 6 for details.
Figure 1:
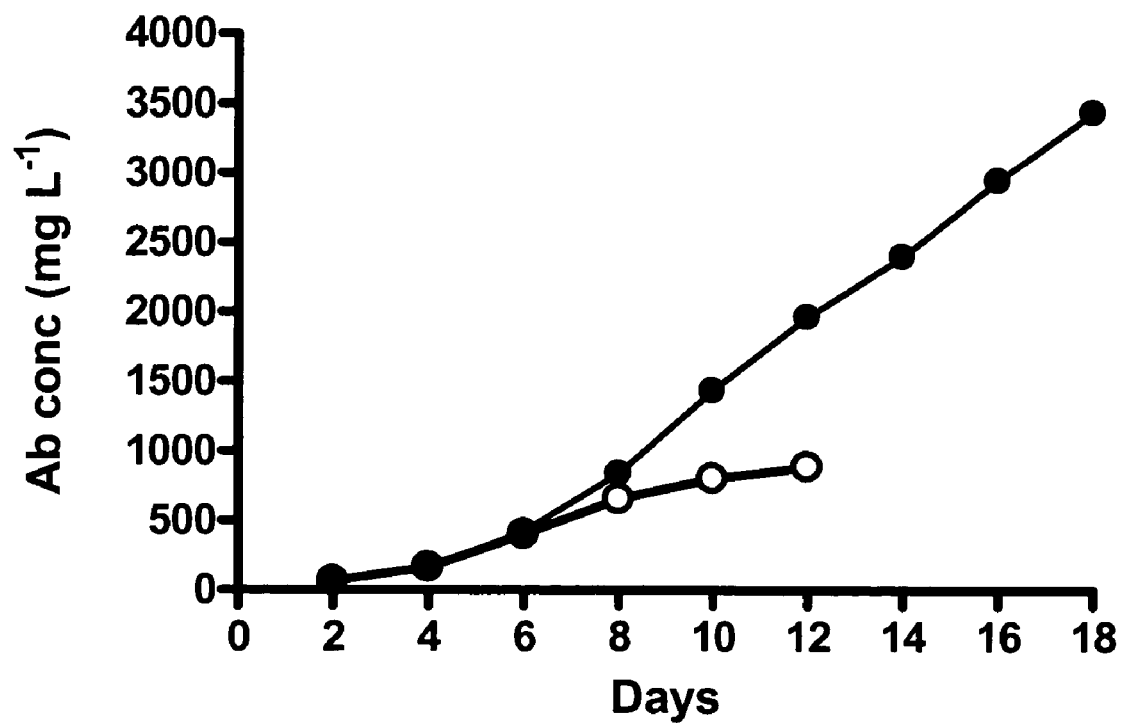

The productivity of any cell line is mainly defined by three basic parameters, the specific productivity of the cell line, the peak viable cell concentration that is attainable and the length of the production process that is possible. Increases in either of these variables will lead to increases in the final product concentration and is dependent to a large extent on the cell line. In a straight batch culture, cell lines such as CHO and SP2/0 can achieve cell densities up to $4 \times 10^6$/ml. In fed-batch or perfusion processes the viable cell concentration is increased, and typically hybridoma cells such as SP2/0 can be cultured up to $10 \times 10^6$ cells/ml, while CHO can be cultured up to $6\text{-}10 \times 10^6$ cells/ml. The invention describes methods to increase the viable cell density of cultures of cells immortalized by adenovirus E1 sequences, preferably, derived from embryonic retina cells, to attain cell densities beyond those reported in the prior art. Furthermore, the methods according to the invention can be used to obtain higher product yields from cultures of cells according to the invention.

Disclosed herein are improvements in how E1-immortalized cells, such as PER.C6 cells (available from Crucell, Leiden, NL), can advantageously be used for the production of high yields of monoclonal antibodies. It is disclosed that these cells be cultured to very high viable cell concentrations in a straight batch process (e.g., up to $14 \times 10^6$ viable cells/ml).

Furthermore, E1-immortalized cells, such as PER.C6 cells, are well suited to a fed-batch process as a culture of these cells unexpectedly consumes lactate and ammonia and maintains viability for long periods of time under nutrient limiting conditions. Methods to increase product yields from the cells by a feed strategy in cultures are provided herein.

With the term "feed strategy" as used herein is meant the addition of certain identified components including but not limited to nutrients, such as sugars, amino acids, and the like, to the culture medium. The identified components are, preferably, added in certain amounts and at certain times, when they are required to improve product yields from the cells, such as provided herein.

E1-immortalized cells, such as PER.C6 cells, are also well suited to a perfusion process as they can be maintained at very high viable cell concentrations (up to $50 \times 10^6$ cells/ml with a viability of at least 85%) for long periods of time and with good final product concentrations.

Culture Media

The processes of the invention generally increase the product yields from the cells compared to yields obtained with processes described in the art for the cells according to the invention. Preferably, serum-free culture media are used at least part of the time in the processes according to the invention. Preferably, the medium contains only recombinantly produced proteins, which are not of animal origin.

Cell culture media are available from various vendors, and serum-free culture media are nowadays often used for cell culture, because they are more defined than media containing serum. The cells of the present invention grow well in serum-containing media as well as in serum-free media. Usually a short period is required to adapt PER.C6 cells from a serum containing medium, such as DMEM+9% FBS, to a serum-free medium. In one embodiment of the invention, EX-CELL™ VPRO culture medium (JRH Biosciences [now SAFC Biosciences], catalog number 14561) is used for the fed-batch or (fed-)perfusion process. In another embodiment, HyQ® CDM4Retino™ (HyClone, catalogue number SH30520) is used. In another embodiment, Mab medium (JRH/SAFC Biosciences) is used. Other serum-free media are available and can be used as well. The cells of the invention in general grow adherently in serum-containing media, but are very proficient in growing in suspension to high cell densities ($10 \times 10^6$ cells/ml and higher) in serum-free culture media, which means that they do not need a surface to adhere to, but remain relatively free from each other and from the walls of the culture vessel during most of the time. Processes for culturing the cells of the invention to high densities and/or for obtaining very high product yields from these cells are described in the incorporated '245 application.

Products

The methods of the invention are, preferably, used to produce products in cells of the invention. The processes of the present invention can be used for the improved production of antibodies, as well as other proteins (WO 00/63403, the contents of which are incorporated by this reference). For the production of proteins, the cells of the invention suitably comprise nucleic acid encoding the proteins, in operable association with elements capable of driving expression of the proteins. Furthermore, the processes can be used for improvement of the production of recombinant adenoviral vectors having a deletion in the E1-region, in which case the cells are used as complementing cells, which in itself is known to the skilled person according to established methodology (e.g., U.S. Pat. No. 5,994,128; WO 01/005945, the contents of both of which are incorporated by this reference). Moreover, the processes according to the invention can be used to improve a process for propagation of other (non-adenovirus) viruses in the cells (WO 01/38362, the contents of which are incorporated by this reference). Hence, products according to the invention can be recombinant proteins, such as antibodies, erythropoietin, and the like, as well as recombinant adenoviral vectors with a deletion in the E1 region, or other viruses.

Cells

The cells according to the invention are cells that have been immortalized with E1 sequences from an adenovirus, which cells are also referred to herein as E1-immortalized cells. Such cells express at least a functional part of the E1A region of an adenovirus, and, preferably, also at least a functional part of the E1B region. E1A protein has transforming activity, while E1B protein has anti-apoptotic activities. The cells according to the invention may be derived from any cell, including lung cells (e.g. human embryonic lung cells, or alternatively A549 cells comprising E1 (see e.g. WO 98/39411), kidney cells (e.g. HEK 293 cells (Graham et al., 1977)), amniocytes (e.g. amniocytes expressing E1 (U.S. Pat.

No. 6,558,948), but preferably, are derived from retina cells. They may preferably be derived from embryonic retina cells. Preferably, the cells according to the invention are human cells. The most preferred cells of the invention are derived from primary human retina cells (human embryonic retina cells, also referred to as HER cells). Immortalization of such cells with adenoviral E1 sequences has for instance been described in U.S. Pat. No. 5,994,128, in Byrd et al, 1982, 1988, and Gallimore et al, 1986. Primary HER cells can be isolated from fetuses (Byrd et al, 1982, 1988). Immortalized HER cells, including the preferred PER.C6 cells, were generated by transfection of primary HER cells using a plasmid that contained the adenovirus serotype 5 (Ad5) E1A- and E1B-coding sequences (Ad5 nucleotides 459-3510) under the control of the human phosphoglycerate kinase ("PGK") promoter (see U.S. Pat. No. 5,994,128).

Accordingly, a preferred cell of the invention can be obtained by methods known to the skilled person. In certain particularly preferred embodiments, the cells of the invention are derived from E1-immortalized HER cells, such as PER.C6 cells. PER.C6 cells for the purpose of the present application shall mean cells from an upstream or downstream passage or a descendent of an upstream or downstream passage of cells as deposited under ECACC No. 96022940. In addition, also the E2A region with a ts125 mutation may be present (see e.g., U.S. Pat. No. 6,395,519, the contents of which are incorporated by this reference) in the cell. A cell derived from a PER.C6 cell can be a PER.C6 cell infected with recombinant adenovirus or other virus, and can also be a PER.C6 cell into which recombinant nucleic acid has been introduced, for instance, comprising an expression cassette wherein nucleic acid encoding a protein of interest is operably linked to sequences capable of driving expression thereof, such as a promoter and polyA signal, wherein, preferably, the cells are from a stable clone that can be selected according to standard procedures known to the person skilled in the art. A culture of such a clone is capable of producing a protein encoded by the recombinant nucleic acid.

In order to achieve large-scale (continuous) production of recombinant proteins through cell culture, it is preferred to have cells capable of growing without the necessity of anchorage. The cells of the present invention have that capability. PER.C6 cells behave better in handling than, for instance, transformed human 293 cells that have also been immortalized by the E1 region from adenovirus. PER.C6 cells have been characterized and have been documented very extensively because they behave significantly better in the process of upscaling, suspension growth and growth factor independence. Especially the fact that PER.C6 cells can be brought in suspension in a highly reproducible manner is something that makes it very suitable for large-scale production. Furthermore, the PER.C6 cell line has been characterized for bioreactor growth in which it grows to very high densities.

The cells according to the invention, in particular PER.C6 cells, have the additional advantage that they can be cultured in the absence of animal- or human-derived serum or animal- or human-derived serum components. Thus isolation is easier, while the safety is enhanced due to the absence of additional human or animal proteins in the culture, and the system is very reliable (synthetic media are the best in reproducibility). Furthermore, the presence of the Early region 1A ("E1A") of adenovirus adds another level of advantages as compared to (human) cell lines that lack this particular gene. E1A as a transcriptional activator is known to enhance transcription from the enhancer/promoter of the CMV Immediate Early genes (Olive et al., 1990, Gorman et al., 1989). When the recombinant protein to be produced is under the control of the CMV enhancer/promoter, expression levels increase in the cells and not in cells that lack E1A.

The cells of the invention contain nucleic acid encoding at least an adenovirus E1A protein in expressible format. In preferred embodiments, the cells further contain nucleic acid encoding at least one adenoviral E1B protein, and preferably both E1B 55K and E1B 19K proteins, in expressible format. The expression of the E1B proteins may prevent apoptosis of the cells. Containing nucleic acid encoding a protein in expressible format means that at least under culture conditions the protein is capable of being expressed.

Components for Feed Strategies

In one aspect, the invention provides processes for culturing cells according to the invention, wherein by feed strategies according to the invention certain amino acids are added during the culturing process to replenish amino acids of which the concentration has become or will become limiting for an optimal process and product yields. By amino acid is intended all naturally occurring alpha amino acids in both their D and L stereoisomeric forms, and their derivatives. A derivative is defined as an amino acid that has another molecule or atom attached to it. Derivatives would include, for example, acetylation of an amino group, amination of a carboxyl group, or oxidation of the sulfur residues of two cysteines to form cystine or vice versa. For instance, cysteine may be rapidly converted into cystine in culture media or during cell culture. Therefore cysteine is considered fully equivalent to cystine for the purpose of the present invention, and cysteine is encompassed within the scope of the term cystine for the purpose of the present application. Further, amino acid derivatives may include esters, salts, such as chlorides, sulphates, and the like, as well as hydrates. It will be understood by the person skilled in the art, that where a specific amino acid is mentioned herein, a derivative may also be used and is meant to be included within the scope of the invention. Other components such as sugars, growth factors, vitamins, etc., may also be added to improve the processes according to the invention.

Feed Strategies

In one aspect, the invention provides a method for producing a product in cells immortalized by adenovirus E1 sequences, in a culture medium, wherein the product is chosen from the group consisting of a recombinant protein, a virus, and a recombinant adenovirus with a deletion in the E1 region, characterized in that the method comprises a step wherein at least leucine, serine, isoleucine, arginine, methionine and cystine are added to the culture medium. In one aspect the invention provides a method for the culturing of cells immortalized by adenovirus E1 sequences, the cells capable of growing in suspension, comprising the steps of: determining at least once during the culturing of the cells the concentration of at least one medium component selected from the group consisting of glucose, glutamine, phosphate, leucine, serine, isoleucine, arginine, methionine, cystine, valine, lysine, threonine and glycine, adding components to the medium during the culturing of the cells at or prior to the depletion of at least one of the components of which the concentration was determined in the previous step, wherein the components added at least comprise glucose, glutamine, phosphate, leucine, serine, isoleucine, arginine, methionine and cystine. "Depletion" as used herein is defined as the time a component has a concentration of 30% or less of the starting concentration in the culture medium. In these aspects, the determination of the concentration of at least one medium component selected from the group consisting of glucose, glutamine, phosphate, leucine, serine, isoleucine, arginine, methionine or cystine is preferred over the determination of only components selected from the group consisting of valine, lysine, threonine and glycine. In certain embodiments, the concentration of at least two medium components according to the invention is determined in the first step. In certain embodiments, the components that are added further comprise one or more of valine, lysine, threonine, glycine, asparagine, tyrosine, histidine, phenylalanine, tryptophan, calcium, LongR3 IGF-1, Long EGF and insulin. In specific embodiments, the components are added in an end concentration in mmoles/l of freshly added component per $10 \times 10^6$ cells/ml of 6.0 for glucose, 2.60 in the first feed and 1.75 in subsequent feeds for glutamine, 0.70 for phosphate, 0.66 for leucine, 1.10 in the first feed and 0.55 in subsequent feeds for serine, 0.50 for isoleucine, 0.46 for arginine, 0.23 for methionine, and 0.25 for cystine. In further embodiments, the following components are further added to an end concentration in mmoles/l of freshly added component per $10 \times 10^6$ cells/ml of 0.45 for valine, 0.44 for lysine, and 0.30 for threonine. In further embodiments, the following components are further added to an end concentration in mmoles/l of freshly added component per $10 \times 10^6$ cells/ml of 0.10 for asparagine, 0.13 for tyrosine, 0.10 for histidine, 0.02 for phenylalanine, and 0.06 for tryptophan. Furthermore, calcium may be added in an end concentration in mmoles/l of freshly added component per $10 \times 10^6$ cells/ml of 0.02. Growth factors such as IGF, EGF, and insulin or their derivatives may also suitable be present in the growth medium. The amounts for the addition of components above may have an error margin per component of 33% or less, preferably, 20% or less, more preferably, 10% or less, even more preferably, 5% or less. The amounts are presented per $10 \times 10^6$ cells/ml, and are linearly dependent on the number of cells/ml. In preferred embodiments, the components are added at between 48 hours and the moment of depletion of at least one of the medium components the concentration of which was determined in the previous step. In certain embodiments, the addition is at a time between 24 hours and just prior to depletion. In certain aspects, the invention provides a method according to the invention, wherein the cells express a recombinant immunoglobulin that is secreted into the culture medium to a level of at least 500 mg per liter, preferably, at least 700 mg/l, more preferably, at least 850 mg/l, even more preferably, at least 1000 mg/l, still more preferably, at least 1250 mg/l, still more preferably, at least 1500 mg/l, still more preferably, at least 1750 mg/l and still more preferably, at least 2000 mg/l. In general, the addition of medium components according to the invention in, for instance, a fed-batch process, results in an increase in the yield of produced product of at least 1.5x, preferably, at least 2x, more preferably, at least 2.5x and still more preferably, about 3x or even higher, compared to the process wherein no components are added, i.e., the batch process.

In addition to glucose in the culture medium and in the feed, galactose may be beneficially present both in the culture medium and in the feed, preferably in a concentration of between about 1 and 50 mM, preferably from 5-30 mM, typically from 10-30 mM. If the culture medium does not contain galactose, it may be beneficially added to the culture medium, preferably in a concentration as indicated. In one embodiment, galactose is added to the culture medium to a starting concentration of 10 mM. Preferably when galactose is present during culturing of the cells, the galactose is also added during the culturing at or prior to the depletion of galactose. This may for instance be done in the form of a culture medium concentrate when the culture medium contains galactose, and/or in the form of free galactose (e.g. when the culture medium does not contain galactose and hence no galactose is present in a culture medium concentrate). The addition of galactose improved the glycosylation pattern of produced proteins containing N-linked glycans. More in particular it generally leads to increased galactosylation and therefore more substrate for sialylation, and hence potentially to increased sialic acid content on the proteins produced by the cells in the culture medium.

In addition to use in a fed-batch process, the feed strategies of the invention can also be beneficially used in an optimized batch process, as set out in Example 5.

Perfusion

Figure 5:
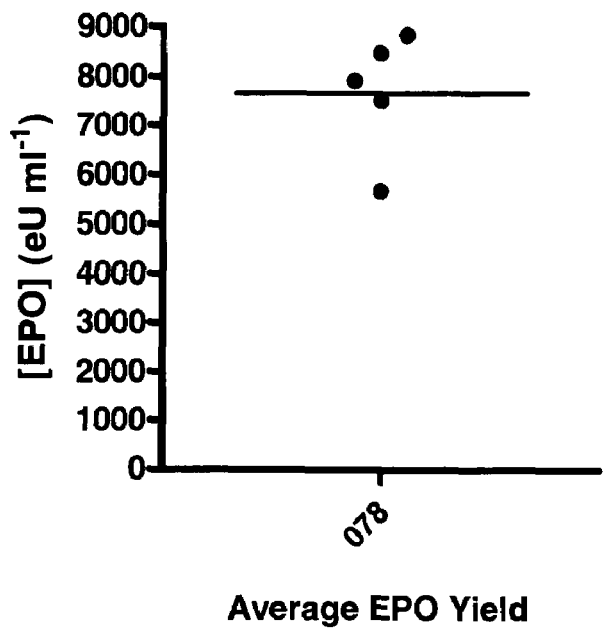
FIG. 5. EPO concentration and average sialic acid content obtained in several runs in a batch process of α-2,3-sialyltransferase over-expressing PER.C6 clone (PER.C6-EPO-ST clone 078). See example 8 for details.
Figure 5:
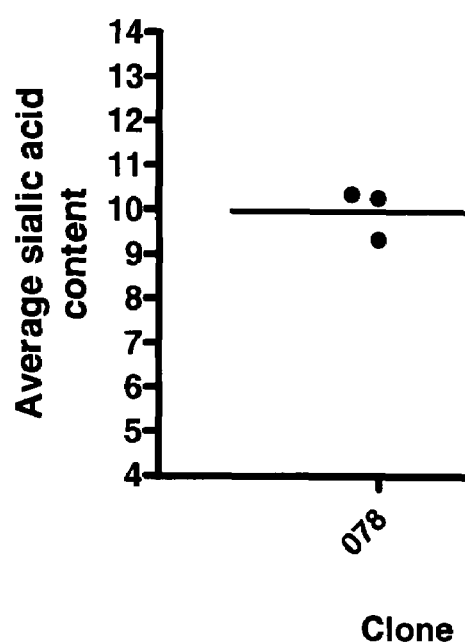

Alternatively, in another aspect of the invention, the entire culture medium may be exchanged. It is shown that unexpected high viable cell densities can be attained when this is applied to cells derived from retina cells immortalized by adenovirus E1 sequences. Exchanging culture medium may be performed by any means known to the person skilled in the art, including, but not limited to, collection of the cells by centrifugation, filtration, and the like, followed by re-suspension of the cells into fresh culture medium. Alternatively, a perfusion system may be used, wherein culture medium is either continuously or intermittently exchanged using a cell separation device such as a Centritech centrifuge or passage through a hollow fiber cartridge, and the like. It is, therefore, another aspect of the invention to provide a process for culturing cells derived from embryonic retina cells immortalized by adenovirus E1 sequences, characterized in that culture medium is exchanged at a rate of 0.2-3, preferably, 0.5-3, culture volumes per day (24 hours). Cultures obtained using this method, preferably, have viable cell densities higher than $20 \times 10^6$ cells/ml, more preferably, higher than $30 \times 10^6$ cells/ml. In certain aspects, such cultures have cell densities higher than $40 \times 10^6$ cells/ml. In certain aspects such cultures are used to produce recombinant antibodies with a yield of at least 150 mg/l/day, preferably, at least 200 mg/l/day, more preferably, at least 300, 400, or 500 mg/l/day. Of course, also other products according to the invention can be produced by such methods. It is shown here that one complete volume exchange of culture medium each day supports at least $30 \times 10^6$ viable cells/ml with antibody yields of more than 500 mg/L/day (up to 750 mg/l/day) (FIG. 5). One complete medium exchange per day corresponds to a continuous perfusion rate of three volumes per day, meaning that a continuous perfusion system could yield approximately at least 150-200 mg/L/day. One method to reduce this perfusion rate and, thus, increase antibody yields (by reducing the volume in which the antibody is secreted) is to supplement the fresh culture medium with the essential components (known as fed-perfusion). These components for antibody-producing E1-immortalized cell, such as PER.C6 cell, clones are identified herein (see Example 2) and therefore it is another aspect of the present invention to provide such a fed-perfusion system, wherein the feed strategies, according to the present invention, are employed. A common drawback of fed-perfusion processes is the build-up of toxic metabolic by-products (such as lactate and ammonia), which can result in low cell viabilities and product yields. There is often a requirement at high cell concentrations for a high perfusion rate to remove these by-products. One advantage demonstrated for E1-immortalized cell, such as PER.C6 cell, clones according to the invention is that they are capable of utilizing lactate and ammonia such that concentrations do not become problematical (see, FIG. 3A). It is, therefore, possible to obtain an antibody yield of at least 500 mg/l/day by changing the culture medium once or twice a day. Alternatively, this can be achieved by using a continuous perfusion rate of for instance one volume per day in combination with supplementation of the medium with a feed concentrate (fed-perfusion). This can advantageously be combined with a cell bleed (removing a certain percentage of the cells population).

Cultures with high cell densities are advantageous for obtaining high product yields. It is, therefore, another aspect of the invention to provide a culture of cells derived from cells immortalized by adenovirus E1 sequences, the culture comprising at least $10 \times 10^6$ cells/ml. The viability in the culture is at least 80%. Preferably, the viability is at least 90%, more preferably, at least 95%. The cultures according to the invention are, preferably, suspension cultures, meaning that the cells in the cultures are in suspension in the culture medium, such as in shake flasks, roller bottles, bioreactors, including stirred tanks, air lift reactors, and the like. The strategies disclosed herein may, however, also be used for cultures of cells in hollow fiber reactors, such as described by Tanase et al. (1997), and for adherent cultures, such as cells on microcarriers. In one embodiment, the culture comprises at least $12 \times 10^6$ cells/ml. It is disclosed herein that up to $14 \times 10^6$ cells/ml can be obtained by a straight batch culture.

It is further demonstrated that, using medium perfusion, even higher cell densities can be achieved, for example, up to $50 \times 10^6$ cells/ml. The prior art does not provide any indication that such unexpected high cell densities are obtainable. In other preferred embodiments, therefore, the invention provides a culture of cells derived from E1-immortalized cells, preferably, derived from retina cells, the culture comprising at least $15 \times 10^6$ cells/ml, preferably, at least $20 \times 10^6$ cells/ml, more preferably, at least $25 \times 10^6$ cells/ml. In specific embodiments, the culture comprises at least $30 \times 10^6$ cells/ml, or even at least $40 \times 10^6$ cells/ml. Cultures with at least $15 \times 10^6$ cells/ml, according to the invention, appear obtainable by a perfusion process, meaning that culture medium is exchanged during the culturing process. The cultures, according to the invention, have a viability of at least 80%, preferably, at least 85%, more preferably, at least 90%, still more preferably, at least 95%. The cultures are suspension cultures. The cultures further comprise growth medium. The growth medium, preferably, is serum-free. The cells of the culture may comprise recombinant nucleic acid molecules encoding immunoglobulins, or parts or derivatives thereof, in expressible format. Such cells are capable of producing immunoglobulins in high yields. In particular, it is shown herein that a culture of cells, according to the invention, wherein the medium is exchanged every day, and wherein more than $30 \times 10^6$ cells/ml are present, can provide recombinant antibody yields of at least 500 mg/l/day. The cells in the culture, preferably, produce at least 10 pg protein/cell/day.

The processes of the invention, especially those for recombinant protein production, can also be combined with other measures described in the art that in some cases improve product yields. Therefore, in certain embodiments of the invention, the culture medium is subjected to a temperature shift before or during the production phase, e.g., by running the process at a lower temperature, for instance, between 30° C. and 35° C., in the production phase (see e.g., U.S. Pat. No. 6,506,598, the contents of which are incorporated herein by this reference, and literature cited therein, which describes effects of lowering the cell culture temperature on several parameters for recombinant protein production), or by the addition of cold culture medium to the culture (wherein cold is meant to be lower than the temperature the cells are cultured in, preferably, the cold culture medium having a temperature between 2° C. and 8° C.) when the cells are subcultured or later during the culture process. In other embodiments, specific growth factors may be added to improve the processes according to the invention with regard to product yields. In yet other embodiments, for the production of proteins, the processes, according to the invention, may be improved by the addition of alkanoic acids or salts thereof, such as sodium butyrate, either during the whole culture phase or only during the production phase (see, e.g., U.S. Pat. No. 6,413,746, and references therein, which describes effects of addition of butyrate on production of proteins in cell culture). In yet other embodiments for the production of proteins, the culture medium is subjected to a temperature or pH shift (Weidemann et al., 1994, Sauer et al., 2000).

It will be clear to the person skilled in the art that several aspects and/or embodiments, according to the invention, can be combined to provide a process for culturing cells which leads to particularly good product yields. As a non-limiting example, it is, for instance, possible to seed a culture of E1-immortalized cells at about $0.8 \times 10^6$ to $2.0 \times 10^6$ cells/ml, and use a feed strategy and/or exchange the growth medium during the culturing process to improve the final product yields.

CA 2309810 A1 (also: WO 99/28346) describes the use of a fed-batch process for the recombinant production in CHO cells and HeLa cells of erythropoietin (EPO) with a high specific activity, characterized by a high proportion of N-acetyl-lactosamine units (lactosamine units) and/or tetra-antennary branches in the carbohydrate structure. It is described therein that a feed containing glucose, galactose and mannose can increase the amount of lactosamine units (repeats) on the N-linked glycans of produced EPO, which is correlated therein with increased biological activity. It is also described therein that there is a correlation between the product of the number of N-acetyl-lactosamine units (LE) and the sialic acid content (SA) and the biological activity: a high value of the product LE×SA is associated with a high biological activity. The fed-batch processes described therein are reported to lead to a cell density of about $3 \times 10^6$ cells/ml and an EPO concentration in the culture medium of 40 mg/l. Fractionation processes are also disclosed therein to obtain EPO compositions with the desired high average amount of lactosamine units and high specific activities (in the range of 200,000 to 450,000 IU/mg protein).

It has been described that it is possible to produce erythropoietin (EPO) in cells of the invention, preferably human embryonic retina cells that have been immortalized by adenovirus E1-sequences, such as PER.C6 cells (see e.g. U.S. Pat. No. 6,855,544, incorporated by reference herein).

Recombinant proteins such as EPO, having N-linked glycosylation, produced in such cells have a specific glycosylation profile, for instance characterized by the presence of Lewis-X structures (described in WO 03/038100, the contents of which are incorporated entirely by reference herein). Another characteristic of the proteins produced thus far in E1A expressing cells appeared a relatively low galactosylation and low sialylation of the N-linked glycans (WO 03/038100). For certain purposes, this may be an advantage, but for other purposes, higher levels of galactosylation and preferably also sialylation may be beneficial. For instance, erythropoietin (EPO) that is produced in cells expressing E1A, has a pronounced number of Lewis-X structures and a relatively low percentage of galactosylation and sialylation in the N-linked glycans (WO 03/038100), resulting in molecules that are less suitable for the treatment of anemia. For the treatment of anemia, it has been established that a high degree of sialylation of EPO is beneficial to increase the half-life of the EPO in serum of treated subjects, and thereby the time when the substance is active in increasing the red blood cell count (Goldwasser et al., 1974). The importance of glycosylation in the biological activity of EPO has been well documented (Delorme et al. 1992; Yamaguchi et al. 1991).

It has also been described that the glycosylation of recombinant proteins, such as EPO, expressed in E1A-expressing cells, such as immortalized human embryonic retina cells, can be altered to increase sialylation, by genetic engineering, i.e. by over-expression of a sialyltransferase in such cells (see e.g. US patent applications published as 2005/0164386 and 2005/0181359, both incorporated herein in their entirety by reference). Preferably, the cells are grown in suspension in serum-free culture medium for expression of the recombinant proteins.

The yields of the processes for production of EPO described in US 2005/0164386 and US 2005/0181359 could be improved. Batch processes were used in those applications, and the present invention provides fed-batch processes combined with measures described in those applications. Strikingly, it is shown herein that the improved yield that can be obtained by the fed-batch processes according to the present invention does not go at the cost of a strong decrease in sialylation of the produced EPO molecules. Therefore, the advantage of the present invention is that it enables the production of high yields of EPO from human embryonic retina cells that express adenovirus E1A protein, while the produced EPO has a high sialic acid content.

The present invention therefore provides a process for recombinant production of erythropoietin (EPO) in a human embryonic retina cell that expresses at least an adenoviral E1A protein, wherein said EPO is produced at a concentration of at least 3000 eU/ml, the process comprising: a) providing an immortalized human embryonic retina cell that expresses at least an adenoviral E1A protein, said cell further comprising a nucleic acid encoding a sialyltransferase under control of a heterologous promoter, and said cell further comprising nucleic acid encoding EPO under control of a heterologous promoter; b) culturing the cell in a serum-free culture medium in a fed-batch process, wherein at least once during said culturing according to needs of nutrients at least one essential amino acid and at least one carbohydrate are added depending on the requirements of the cells; and c) harvesting EPO from the culture medium, wherein the EPO is present in the culture medium at a concentration of at least 3000 eU/ml.

Said EPO as produced has an average sialic acid content per EPO molecule of at least 7, preferably at least 8. Strikingly, it has been observed that there was no significant decrease of the average sialic acid content per EPO molecule as produced by the fed-batch process according to the invention as compared to the batch process; in fact, there is even a slight increase. This is unexpected, because it has previously been reported that certain culture conditions often encountered at the end of fed-batch processes (for example high ammonia concentrations) can result in a decreased sialylation of the expressed glycoprotein (Andersen and Goochee 1995, Gawlitzek et al 2000).

Indeed, for the expression of antibodies it has been observed that the feed-strategies of the invention lead to a slight decrease in galactosylation (see the incorporated '245 application). It is therefore an aspect of the invention to provide a fed-batch process for recombinant expression of EPO according to the invention, wherein the average sialic acid content of the EPO as produced is at least 90%, preferably at least 95%, more preferably at least 98%, still more preferably at least 100% as compared to the batch process.

For the concentration of EPO as produced in the culture medium in a fed-batch process of the invention, values of between about 4000 and about 6000 eU/ml were observed with a clone that over-expresses the α-2,6-sialyltranferase together with EPO. The improvement in yield of EPO when compared to a batch process was observed to be about 6.5-fold, which is strikingly higher than that obtained for recombinant antibodies (about 3-fold, see the incorporated '245 application). It is, therefore, an aspect of the invention to provide a process for recombinant expression of EPO, the process comprising the feed strategy, according to the invention, wherein the yield of a produced protein is increased at least 3-fold, preferably at least 4-fold, more preferably at least 5-fold, still more preferably at least 6-fold, over the yield in the batch process. For a batch process with a clone that over-expresses the α-2,3-sialyltranferase together with EPO, values of the EPO concentration as produced in the culture medium were observed of about 8000 eU/ml. When a similar increase in yield (6.5-fold) would be observed as observed for the clone with the α-2,6 sialyltransferase in a fed-batch process, the yields would be approximately 52,000 eU/ml, which would be extremely high for recombinant EPO expression. Possibly, upon screening other clones with even higher yields might be obtained. In preferred embodiments of the invention, the EPO is produced at a concentration of at least 4000 eU/ml of culture medium, more preferably at least 5000 eU/ml. Typically, the EPO concentration as produced will be between 3000 and 100000 eU/ml, more typically between 3000 and 60000 eU/ml. Preferably, the EPO concentration as produced will be between about 5000 and 100000 eU/ml, typically between about 5000 and 60000 eU/ml. For the ELISA used (Quantikine® IVD® Erythropoietin ELISA, R&D Systems Inc., Catalog number DEP00), 1 eU corresponds to about 5-10 ng, more typically to about 6-8 ng for the EPO molecules obtained by the processes of the invention.

In step b) of the processes according to the invention, the feed strategies as disclosed in the incorporated '245 application is applied. In preferred embodiments of the process according to the invention, said at least one essential amino acid and at least one carbohydrate at least comprise glucose, glutamine, phosphate, leucine, serine, isoleucine, arginine, methionine and cystine. Preferably, at least one further component is added to the culture medium, wherein the further component comprises one or more of valine, lysine, threonine, glycine, asparagine, tyrosine, histidine, phenylalanine, tryptophan, phosphate, calcium, LongR3 ME-1, Long EGF and insulin. Preferably, before addition of the components, during the culturing of the cells the concentration of at least one medium component selected from the group consisting of glucose, glutamine, phosphate, leucine, serine, isoleucine, arginine, methionine, cystine, valine, lysine, threonine and glycine is determined at least once. The components are added to the medium during the culturing of the cells at or prior to the depletion of at least one of the components of which the concentration was determined. Preferably, the components are added in an end concentration in mmoles/l of freshly added component per $10 \times 10^6$ cells/ml of between 4.0 and 8.0 for glucose, 0.44 and 0.88 for leucine, 0.37 and 1.47 for serine, 0.33 and 0.67 for isoleucine, 0.31 and 0.61 for arginine, 0.15 and 0.31 for methionine, and 0.1 and 0.6 for cystine. Preferably, glutamine is added to an end concentration of between 1.17 and 3.47 mmoles/l of freshly added glutamine per $10 \times 10^6$ cells/ml. Preferably, the components are added more than one time, and preferably further such that, as a result of the first addition, the end concentration of freshly added glutamine is higher than as a result of a subsequent addition. In certain other embodiments, glutamine is added essentially continuously such that the residual concentration of glutamine in the medium is maintained between 0.2 and 1.5 mM or between 0.5 and 1.0 mM. Preferably, the following components are added to an end concentration in mmoles/l of freshly added component per $10\times10^6$ cells/ml of between 0.3 and 0.6 for valine, 0.29 and 0.59 for lysine, 0.2 and 0.4 for threonine. Preferably, the following components are added to an end concentration in mmoles/l of freshly added component per $10\times10^6$ cells/ml of between 0.067 and 0.13 for asparagine, 0.087 and 0.17 for tyrosine, 0.067 and 0.13 for histidine, 0.013 and 0.027 for phenylalanine, and 0.04 and 0.08 for tryptophan.

In certain preferred embodiments, galactose is also present in and/or added to the culture medium, preferably in a concentration of between about 1 and 50 mM, more preferably from about 5-30 mM, e.g. 10 mM.

In preferred embodiments, the fed-batch process is harvested at a time between 8 and 20 days (from the start of the fed-batch culture). It is expected that after 8 days already some increase in yield will be obtained as compared to the batch process, whereas processes longer than 20 days suffer from a decrease in quality of the EPO obtained, e.g. the obtained EPO will then contain a lower average sialic acid content. Preferably the fed-batch process is harvested at a time at a time between 10 and 15 days, more preferably at a time between 11 and 14 days. In certain embodiments, the fed-batch process is harvested after about 12 days.

In certain aspects, the process of the invention further comprises at least one step of separation of undesired components from the produced EPO molecules while enriching EPO molecules which contain an increased number of sialic acids per molecule, to obtain EPO with an average sialic acid content per EPO molecule of at least 12.

The invention further provides a process for recombinant production of erythropoietin (EPO) in a human embryonic retina cell that expresses at least an adenoviral E1A protein and further obtaining a desired fraction of EPO, wherein said EPO is produced at a concentration of at least 3000 eU/ml, the process comprising: a) providing a human embryonic retina cell that expresses at least an adenoviral E1A protein, said cell further comprising a nucleic acid encoding a sialyltransferase under control of a heterologous promoter, and said cell further comprising nucleic acid encoding EPO under control of a heterologous promoter; b) culturing the cell in a serum-free culture medium in a fed-batch process, wherein at least once during said culturing according to needs of nutrients at least one essential amino acid and at least one carbohydrate are added depending on the requirements of the cells; c) harvesting EPO from the culture medium, wherein the EPO is present at a concentration of at least 3000 eU/ml; and d) separation of undesired components from the produced EPO molecules while enriching EPO molecules which contain an increased number of sialic acids per molecule, to obtain EPO with an average sialic acid content per EPO molecule of at least 12.

Methods to produce proteins in host cells are well established and known to the person skilled in the art. The use of immortalized HER cells for this purpose is described in WO 00/63403.

In general, the production of a recombinant protein in a host cell comprises the introduction of nucleic acid in expressible format into the host cell, culturing the cells under conditions conducive to expression of the nucleic acid and allowing expression of the said nucleic acid in said cells.

Alternatively, a protein that is naturally expressed in desired host cells, but not at sufficient levels, may be expressed at increased levels by introducing suitable regulation sequences such as a strong promoter in operable association with the desired gene (see e.g. WO 99/05268, where the endogenous EPO gene is overexpressed by introduction of a strong promoter upstream of the gene in human cells).

Nucleic acid encoding a protein in expressible format may be in the form of an expression cassette, and usually requires sequences capable of bringing about expression of the nucleic acid, such as enhancer(s), promoter, polyadenylation signal, and the like. Several promoters can be used for expression of recombinant nucleic acid, and these may comprise viral, mammalian, synthetic promoters, and the like. In certain embodiments, a promoter driving the expression of the nucleic acid of interest is the CMV immediate early promoter, for instance comprising nt. −735 to +95 from the CMV immediate early gene enhancer/promoter, as this promoter has been shown to give high expression levels in cells expressing E1A of an adenovirus (see e.g. WO 03/051927). The nucleic acid of interest may be a genomic DNA, a cDNA, synthetic DNA, a combination of these, etc.

Erythropoietin (EPO) according to the invention preferably is human erythropoietin, or a fragment of human erythropoietin, or a mutein of human erythropoietin. Such an erythropoietin should preferably be biologically active, which means that it should have at least one of the following activities: a) causing bone marrow cells to increase production of reticulocytes and red blood cells, increase hemoglobin synthesis or iron uptake (see e.g. U.S. Pat. No. 4,703,008), and/or b) responsive cellular protective activity selected from the group consisting of protecting, maintaining, enhancing or restoring the function or viability of a responsive mammalian cell, tissue or organ, such as for instance disclosed in WO 00/61164 and WO 02/053580. The sequence of human erythropoietin is well known (e.g. U.S. Pat. No. 5,441,868; EP patent 0411678, cDNA: Genbank accession number: MI 1319). EPO muteins, analogues, peptides, or fragments binding the EPO receptor and having some kind of activity associated with EPO have for instance been described in U.S. Pat. Nos. 5,457,089, 4,835,260, 5,767,078, 5,856,292, 4,703,008, 5,773,569, 5,830,851, 5,835,382, and international publications WO 95/05465, WO 97/18318 and WO 98/18926, all incorporated by reference for the purpose of disclosing EPO fragments and EPO muteins having biological activity. The EPO of the invention may also be modified, as for instance disclosed in WO 02/053580, e.g. by carbamylation of one or more lysines in the EPO molecule (see e.g. WO 02/053580, Leist et al, 2004): such modified EPO has no significant erythropoietic activity, but retains its tissue protective activity. Certain EPO mutants have also been found to have these properties (Leist et al, 2004), such as EPO with a mutation of serine to glutamate at position 100 (EPO-S100E) and EPO with a mutation of arginine to glutamate at position 103 (EPO-R103E). Lists of these and other EPO mutants have been disclosed in WO 2004/003176, incorporated herein by reference. All these modified EPO molecules and all these muteins are included within the scope of erythropoietin according to the present invention. In certain embodiments, EPO is human EPO, which contains four carbohydrate chains. Three of these contain N-linkages to asparagines, and one contains an O-linkage to a serine residue. The importance of glycosylation in the biological activity of EPO has been well documented (Delorme et al. 1992; Yamaguchi et al. 1991).

Recombinant proteins, such as recombinant human erythropoietin (EPO), produced in PER.C6 cells may be poorly sialylated due to a low incorporation of Gal and due to the presence of $\alpha$1,3-linked fucoses. The addition of sialic acids to terminal Gal or GalNAc in N-linked glycans is mediated by sialyltransferases. Methods have been described in US 2005/0164386 to increase the sialic acid content of proteins produced in PER.C6 cells. The increased level of sialylation is obtained in two steps: the first step involves the increase in the level galactosylation in order to provide more (acceptor) sites for sialylation. An increase in the level of galactosylation was found to occur when PER.C6 cells were grown in suspension in a serum-free culture medium. The second step involves the increase the cell's potential to catalyze the process of sialylation, which was accomplished by the over-expression of a sialyltransferase. By combining these measures, the forming of mature N-linked sugars that are sialylated was dramatically improved (see US 2005/01644386 and US 2005/0181359). These measures are also taken in the present invention, to obtain EPO with a high sialic acid content.

Commercial EPO preparations are usually recombinantly produced in CHO or BHK cells, and fractions containing a high degree of sialylation are isolated, because increased sialylation is beneficial for the half-life of the protein and therefore for the capability to exert its therapeutic effect of increasing hemoglobin and red blood cell counts. The methods described in US 2005/01644386 and US 2005/0181359 provide the possibility to use immortalized HER cells that express adenoviral E1A for the recombinant production of EPO with increased half-life by co-expression of EPO with a sialyltransferase (the sialyltransferase being under control of a heterologous promoter) as compared to the same cells without concomitant overexpression of a sialyltransferase.

Of course, also the EPO or other proteins produced in the E1A containing HER cells that overexpress a sialyltransferase, can be fractionated to obtain further fractions with still higher sialic acid contents (see e.g. US 2005/0164386), as is also done for commercial preparations of EPO. In one aspect, the EPO produced according to the invention, is purified using an anion exchange column to obtain highly sialylated fractions. Methods to purify and further fractionate EPO compositions, enriching for EPO that on average has an increased sialic acid content per EPO molecule, are known to the person skilled in the art and include for instance anion exchange chromatography, preparative iso-electric focusing (IEF), chromatofocusing, affinity chromatography e.g. using lectins, capillary zone electrophoresis (CZE), etc. It is shown in the present application that indeed EPO with an average sialic acid content higher than 12 can be obtained from material produced in E1A expressing cells that also over-express a sialyltransferase (see e.g. Example 9 below).

The concept of genetic engineering to alter glycosylation of recombinant proteins produced in a cell has been amply established, and is for instance discussed in detail in U.S. Pat. No. 5,047,335. Subsequent work has established that glycosylation engineering is applicable to the production of recombinant proteins in host cells (e.g., Grabenhorst et al., 1995; Jenkins et al, 1998; Weikert et al, 1999). Hence, the methods for genetic engineering of glycosylation are well established and known to the person skilled in the art, and can as such be used according to the present invention. Indeed, the cells and methods for increasing sialylation of EPO produced in E1A-expressing HER-cells have been described and are thus available to the skilled person (US 2005/01644386 and US 2005/0181359).

To this purpose, nucleic acid encoding the desired glycosylation enzyme in expressible format is or has been introduced into the cells according to the invention, and the desired glycosylation enzyme is expressed during the culturing of the cells according to the invention when the protein of interest is expressed. This results in an altered glycosylation pattern of the protein of interest as compared to the situation when no recombinant glycosylation enzyme is expressed in the cells. In preferred embodiments, the glycosylation enzyme is a sialyltransferase. The sialyltransferase used is preferably a mammalian sialyltransferase, more preferably a human sialyltransferase. In preferred embodiments, the sialyltransferase is chosen from the group consisting of alpha-2,6-sialyltransferases and alpha 2,3-sialyltransferases. The nucleic acid encoding the desired glycosylation enzyme preferably is under control of a heterologous promoter, which should be active or have the possibility of being regulated in the cells of the invention. Preferably, the nucleic acid encoding the glycosylation enzyme is integrated into the genome of the cells, to ensure stable inheritance, and provide for stable expression of the enzyme in subsequent generations of the cells. The expression of the sialyltransferase increases the sialylation of recombinant proteins in those cells. Moreover, when the E1A-expressing cells expressing the sialyltransferase are grown in suspension in serum-free culture media, a clear and significant increase in sialylation of the N-linked glycans of a recombinant protein that is expressed in these cells is observed. Hence, in preferred embodiments of the processes according to the present invention, the cells according to the invention comprise nucleic acid encoding a sialyltransferase, such as alfa-2,6-sialyltransferase, in expressible format, for instance under control of a heterologous promoter, i.e. a promoter that is not the natural promoter of the gene encoding the glycosylation enzyme. A suitable $\alpha$-2,6-sialyltransferase is a human $\alpha$-2,6-sialyltransferase, the sequence of which was described by Grundmann et al, 1990.

In another preferred embodiment, the cells comprise nucleic acid encoding an alfa-2,3-sialyltransferase, in expressible format, for instance under control of a heterologous promoter. The alfa-2,3-sialyltransferase may be the human $\alpha$-2,3-sialyltransferase, known as SIAT4C or STZ (Genbank accession number L23767, see also U.S. Pat. No. 5,494,790).

The introduction of nucleic acid encoding a sialyltransferase into immortalized HER cells expressing E1A has previously been described (e.g. US 2005/0164386 and US 2005/0181359).

Methods described in US 2005/01644386 and US 2005/0181359 can provide compositions comprising one or more isoforms of an erythropoietin (EPO) comprising glycans linked thereto, wherein said glycans comprise on average at least 6 sialic acid moieties per EPO molecule. A mixture of such isoforms can be obtained by producing EPO in PER.C6 cells that further overexpress a sialyltransferase, and which is cultured in suspension in serum-free medium. The composition is generally obtained as a mixture of EPO isoforms, but the person skilled in the art could isolate the separate isoforms, as described in U.S. Pat. No. 5,856,298, in particular example 1 therein. Compositions comprising on average at least 7 sialic acid moieties per EPO molecule, or at least 8 sialic acid moieties per EPO molecule could also be obtained. The sialic acid moieties are mainly present as terminal sialic acids on N-linked glycans, but some sialic acids might be present on O-linked glycans and contribute to the average sialic acid content of the composition. The described EPO molecules in certain embodiments comprise 3 N-linked glycans, more typically 3 N-linked glycans and one O-linked glycan.

The present invention can in principle provide similar compositions of EPO molecules, however these are obtained in significantly improved quantities. The current invention therefore provides methods to produce high yields of EPO with high sialic acid content.

The obtained EPO compositions (with an average sialic acid content per EPO molecule of at least 8) can be used to further purify and obtain even more preferred (fractionated)

compositions, having average sialic acid content that is still higher, e.g. comprising on average per EPO molecule at least 10 sialic acids, preferably at least 11 sialic acids, more preferably at least 12 sialic acids. Typically, such fractionated compositions comprise on average per EPO molecule between about 10 and 15 sialic acids, preferably between 11 and 15 sialic acids, more preferably between 12 and 15 sialic acids. More typically, such fractionated compositions comprise on average per EPO molecule not more than 14 sialic acids. Upon separation, EPO fractions can thus for instance be obtained that comprise on average from about 12 to about 14 sialic acid moieties per EPO molecule. For comparison, a commercially available EPO preparation analysed in the same manner on average contained about 12.4 sialic acids per EPO molecule. Methods and means to perform such purification and fractionation are available in the art, e.g. anion exchange chromatography, preparative isoelectric focusing and the like.

In certain embodiments, the EPO compositions obtained after fractionation comprise from 1 through 6 isoforms, more typically from 2 through 5 isoforms, still more typically 2, 3 or 4 isoforms, together accounting for at least 70%, preferably at least 80%, more preferably at least 90%, of the EPO present in said composition.

The present invention is exemplified by erythropoietin as an example of a recombinant protein, but it will be appreciated by the person skilled in the art that the methods including the feed strategies disclosed herein could also be applied for recombinant expression of other glycoproteins, to increase the yields thereof while at the same time obtain preparations of such glycoproteins with advantageous glycosylation profiles, e.g. characterized by a high level of sialylation.

The invention will now be illustrated with some examples, not intended to limit the scope of the invention.

Experimental

Methods and vectors for genetically engineering cells and/or cell lines to express a protein of interest are well known to those of skill in the art; for example, various techniques are illustrated in Current Protocols in Molecular Biology, Ausubel et al., eds. (Wiley & Sons, New York, 1988, and quarterly updates) and Sambrook et al., Molecular Cloning: A Laboratory Manual (Cold Spring Laboratory Press, 1989). General and standard cell culture techniques are known to the person skilled in the art, and are, for instance, described in R. I. Freshney, Culture of animal cells: A manual of basic technique, fourth edition (Wiley-Liss Inc., 2000, ISBN 0-471-34889-9). Such standard techniques were followed unless otherwise noted.

Cell Culture Protocols

PER.C6 cells were cultured in the examples. Cells were adapted from adherent cultures in DMEM containing 10% FBS (Invitrogen) to serum-free medium by direct transfer. Briefly, sub-confluent, logarithmic cells were trypsinized, washed once with serum-free medium and inoculated directly into 250 ml Erlenmeyer flasks with a 0.2µ filter (Corning), containing 25 ml of ExCell-525 serum-free medium (JRH Biosciences) at a starting cell concentration of $0.3$-$0.5 \times 10^6$ ml$^{-1}$, unless otherwise noted. Cultures were maintained in logarithmic growth in Erlenmeyer flasks by passage every two to three days. Flasks were shaken on a magnetic shaker platform (Infors) at 100 rpm in a humidified incubator at 37° C. and 5% $CO_2$. Cultures were passaged by centrifugation at 1000 rpm for 5 minutes. The supernatant was removed and the pellet re-suspended in the remaining medium. Fresh, cold medium (4° C.) was added and new flasks inoculated at the appropriate cell concentration. After transfer to serum-free medium, cultures were passaged for two to four weeks to allow for complete adaptation, after which a serum-free cell bank was created. All experiments were started using cells from this cell bank.

Bioreactors

Bioreactor cultures were performed in 3L reactors with a 2L working volume (Applikon). Temperature was maintained at 37° C. by a heating blanket. Dissolved oxygen concentration ($dO_2$) was controlled at 50% of air saturation by adjusting inlet gas composition through the headspace and intermittent sparging through a microporous sparger. Starting culture pH was controlled at 7.3 by $CO_2$ addition through the microporous sparger. The lower culture pH limit was set at 6.7 so that the culture pH was allowed to drift downwards (the lower limit was not reached). Cultures were agitated by two marine impellers at 75 rpm. Process data was acquired by the BioExpert software (Applikon).

Analytical Protocols

Cell counts and viability measurements were performed using a CASY automatic cell counter (Schärfe Systems). Glucose, lactate, ammonia and phosphate concentrations were determined using an EKTACHEM II® analyzer (Kodak) with cell-free culture supernatants. Amino acid concentrations were determined using a modified AccuTag HPLC method (Waters) as described by van Wandelen and Cohen (1997). Aliquots (200 µl) of centrifuged culture supernatant were stored at −20° C. in 1 ml cryovials (Nalgene) until required. Samples from each experiment were analyzed at the same time to avoid experimental variation. Osmolality was measured by a freezing point depression osmometer (Osmomat 030-d, Gonotec). Antibody concentration was determined by a sandwich-type ELISA. Briefly, plates were coated with 2 µg ml$^{-1}$ mouse anti-human IgG against the kappa light chain (Pharmingen) and incubated overnight at 4° C. An HRP-conjugated mouse anti-human IgG against the heavy chain (Pharmingen; 1:500) was used as detection antibody for one hour at 37° C. with OPD (Sigma) as substrate. Washing between incubation steps was performed with 0.05% Tween 20 in PBS. Samples were diluted in washing buffer supplemented with 0.1% BSA. Quantification was relative to an IgG1 reference standard using a calibration range of 10 to 400 ng ml$^{-1}$. Antibody samples purified by Protein A were subject to quality analysis by isoelectric focusing (IEF) and denaturing polyacrylamide gel electrophoresis (SDS-PAGE). For glycan analysis, N-linked glycans were removed by PNGase F treatment of the IgG samples in 20 mM sodium phosphate (pH 7.2) and analyzed with MALDI-MS in the reflector mode on an Applied Biosystems Voyager DE Pro mass spectrometer. The matrix was 2,5-dihydroxybenzoic acid (10 mg ml$^{-1}$) in 50/50/0.1 acetonitrile/water/trifluoroacetic acid. Spectra were obtained in the positive ion mode and glycans were detected as sodium adducts, [M+Na]+.

Calculation of Cell Specific Metabolic Rates

Cell specific rates of metabolite utilization and production in batch and fed-batch culture were calculated using the log mean of the cell concentration as shown in the following equation:

$$q_s = (C_2 - C_1)/(t_2 - t_1) \times [(X_2 - X_1)/\ln(X_2 - X_1)].$$

In this equation, C is the metabolite concentration (µmoles/l), t is time (days) and X is the viable cell concentration. A rate constant accounting for the spontaneous decomposition of glutamine was not included as decomposition was not significant at the time points at which the rates were calculated (data not shown). The yield coefficients of lactate produced per glucose ($Y_{lac/glc}$), ammonia produced per glutamine ($Y_{amm/gln}$) and alanine produced per glutamine ($Y_{ala/gln}$) were calculated from the equations below and are expressed in mole/mole:

$$Y_{lac/glc} = q_{lac}/q_{glc}$$

$$Y_{amm/gln} = q_{amm}/q_{gln}$$

$$Y_{ala/gln} = q_{ala}/q_{gln}$$

EXAMPLES

Example 1

Increasing Maximum Final Cell Yields in Batch Culture of PER.C6 Cells

The simplest production process is a batch culture. However, this is restricted in the viable cell concentration and therefore the product yields attainable, due largely to nutrient limitation. A method is presented to increase the maximum final cell concentration of a batch culture of PER.C6 or PER.C6-derived sub-clones by calculating the cell specific rate of utilization of key nutrients at different cell concentrations and starting the batch culture at a cell concentration where there is optimal utilization of nutrients with respect to cell growth.

The DNA encoding the antigen-binding region of an antibody recognizing epithelial cell adhesion molecule (EpCAM) was first isolated from a scFv phage display library (Huls et al., 1999). DNA encoding the antigen-binding region of an antibody recognizing CD46 was isolated as disclosed in WO 02/018948, the contents of which are incorporated by this reference. A leader sequence and constant regions of IgG1 type were added essentially as described in Boel et al., 2000. The DNA encoding the light and heavy chains were then cloned into expression vector pcDNA3002(Neo). The expression vector pcDNA3002(Neo), which has been described in international patent application PCT/NL02/00841, was deposited on Dec. 13, 2001, at the European Collection of Cell Cultures (ECACC) under Number 01121318. The resulting expression vectors, encoding an IgG1 that recognizes EpCAM or CD46, respectively, regulated by a CMV promoter, was introduced in PER.C6 cells according to standard methods.

A recombinant antibody-expressing clone, derived from a parental population of the PER.C6 cell line, was used in these experiments. The clone expressing anti-EpCAM is further referred to herein as clone 1, the clone expressing anti-CD46 is further referred to herein as clone 2.

Cells were maintained in EXCELL™ 525 medium (JRH Biosciences) (maintenance of the cells in G™-3 medium (Sigma) did also work) and batch productions were carried out in EXCELL™ VPRO medium (JRH Biosciences, Cat. No. 14560). Cells were transferred directly from EXCELL™ 525 to EXCELL™ VPRO for the batch productions.

FIG. 1 of the incorporated '245 application shows that the maximum final viable cell concentration of cultures started at $1 \times 10^6$ cells ml$^{-1}$ reached almost $14 \times 10^6$ cells ml$^{-1}$ after six days (approximately three-fold higher than batch cultures of CHO and Sp2/0), compared to cultures started at $0.3 \times 10^6$ ml$^{-1}$, which reached $10 \times 10^6$ cells ml$^{-1}$ after nine days. There is very little difference in the final antibody titers of both cultures. However, in the culture started at $1 \times 10^6$ ml$^{-1}$, approximately 600 mg L$^{-1}$ was reached after six days, compared to nine days for the cultures started at $0.3 \times 10^6$ ml$^{-1}$.

The higher cell concentrations observed in cultures started at $1 \times 10^6$ cells ml$^{-1}$ compared to $0.3 \times 10^6$ ml$^{-1}$ is due to the lower cell specific rate of nutrient utilization at the higher cell concentration. The respiration rate of hybridoma cells has been shown to decrease with increasing cell density (Wohlpart et al., 1990). Similarly, the cell specific rate of utilization of a nutrient has also been shown to decrease with increasing cell concentration (Portner et al., 1994, Yallop and Svendsen 2001). We have now used this information in a novel and inventive way to form a concept for increasing attainable cell densities in a culture.

Figure 2:
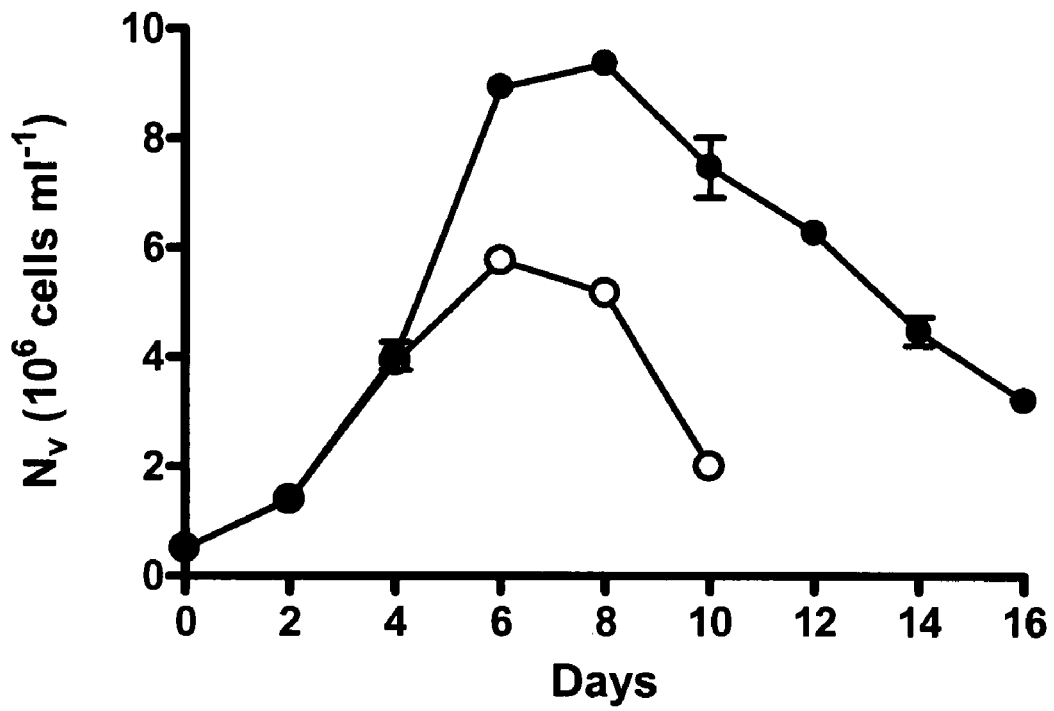
FIG. 2. Viable cell numbers ($N_v$) and antibody (Ab) concentration obtained in a batch (open circles) and a fed-batch (closed circles) process for antibody expressing clone 4b. See example 6 for details.
Figure 2:
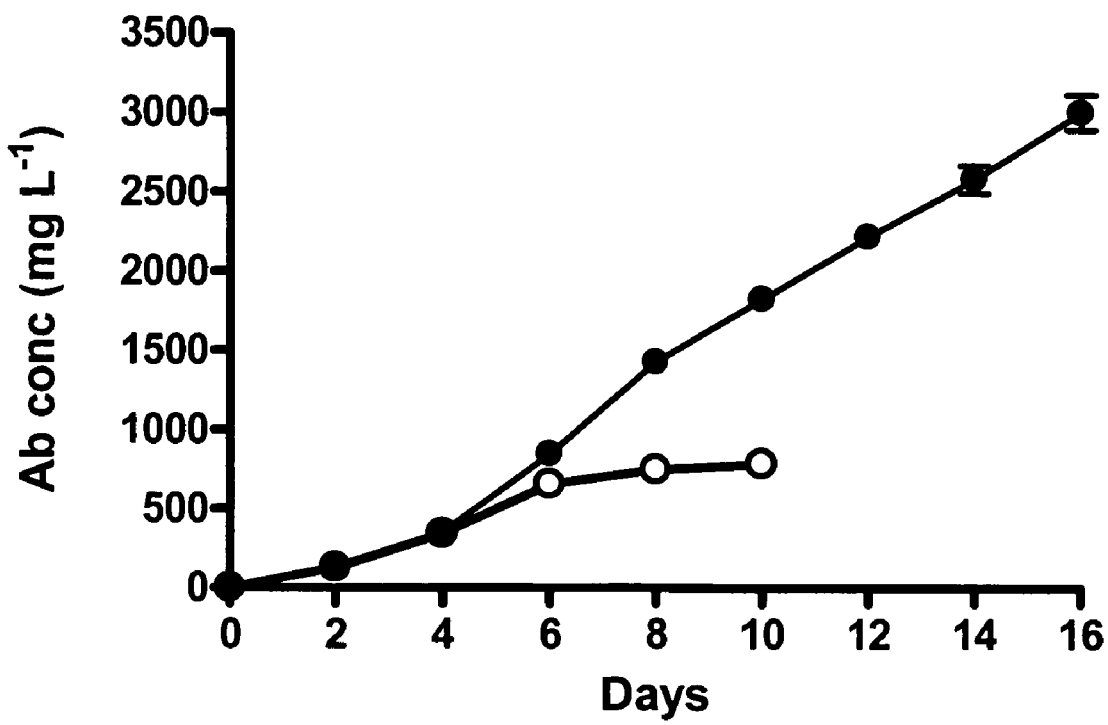

By calculating the cell specific rate of utilization of a key nutrient each day in a batch culture and plotting these values against cell concentration, a graph can be obtained as shown in FIG. 2 of the incorporated '245 application for glutamine. FIG. 2 of the incorporated '245 application shows the relationship between the cell specific rate of glutamine utilization ($q_{Gln}$) and cell concentration. From this graph, an optimum starting cell concentration can be selected based on optimal use of the available nutrients. For example, a culture starting at $0.3 \times 10^6$ cells ml$^{-1}$ will reach approximately $0.5 \times 10^6$ m$^{-1}$ in 24 hours (average population doubling time (pdt) of this clone is 32 hours). The $q_{Gln}$ value at $0.5 \times 10^6$ cells ml$^{-1}$ is approximately 2.5 µmoles $10^6$ cells$^{-1}$ 24 hours$^{-1}$. The total glutamine consumed in this 24 hours will, therefore, be approximately 1.25 µmoles ml$^{-1}$ (0.5×2.5). However, a culture starting at $1 \times 10^6$ cells ml$^{-1}$ will reach approximately $1.5 \times 10^6$ ml$^{-1}$ in 24 hours. The $q_{Gln}$ value at this cell concentration is approximately 0.75 µmoles $10^6$ cells$^{-1}$ 24 hours$^{-1}$. The total glutamine consumed will therefore be approximately 1.125 µmoles ml$^{-1}$. The two cultures will therefore use approximately the same amount of glutamine in the first 24 hours.

It is, therefore, another object of the invention to provide a method of culturing cells, comprising starting a culture at a cell concentration where the specific nutrient utilization level is close to a minimum plateau level. This equates with around 0.8 to $2.0 \times 10^6$ cells/ml, preferably, $0.9$-$1.5 \times 10^6$ cells/ml, for E1-immortalized retina cells, particularly PER.C6-derived cells. It is, therefore, an embodiment of the invention to subculture the cells at a seeding concentration of $0.8$-$2.0 \times 10^6$ cells/ml, preferably, $0.9$-$1.5 \times 10^6$ cells/ml, more preferably, $0.95$-$1.25 \times 10^6$ cells/ml.

The advantage of this aspect of the invention is that the number of viable cells that can be obtained is higher at this higher seeding density, and higher numbers of cells are reached faster during the process. This aspect of the invention, therefore, is very useful for batch cultures, but can also be beneficially used in fed-batch cultures or (fed-) perfusion cultures, such as those of the present invention.

Example 2

Feed Strategies for Improving Antibody Yields in PER.C6 Derived Sub-Clones

Fed-batch processes aim at increasing product yields by increasing the viable cell concentration or prolonging the production period by feeding nutrient concentrates to replenish those that are consumed. We present here a feed strategy for improving the antibody yields of PER.C6 derived sub-clones. The feed strategy can be combined with a higher starting cell density to obtain a higher final cell density at the onset of the nutrient feed and a shorter overall production process.

Figure 3:
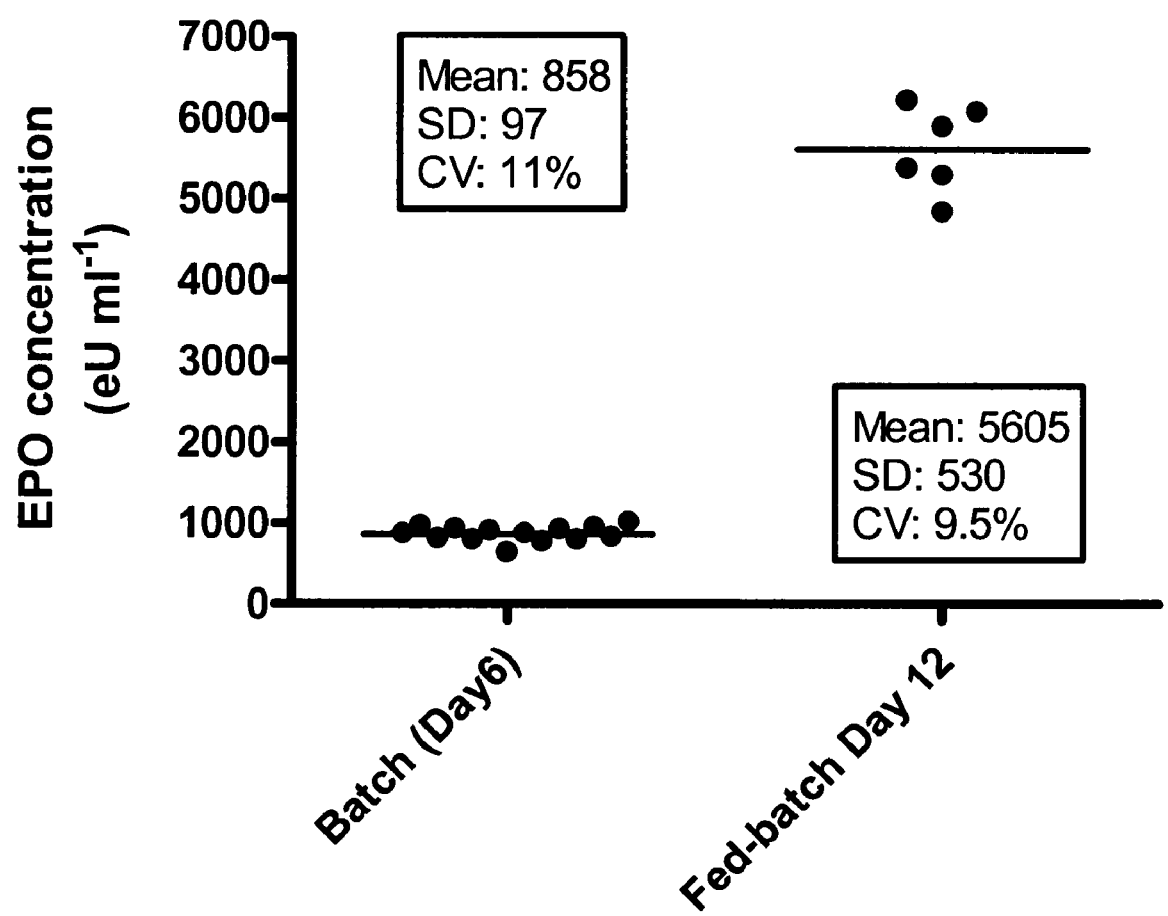
FIG. 3. EPO concentration obtained in several runs of a batch process at day 6 and of a fed-batch process according to the invention at day 12. Dots indicate data points of separate runs, the line represents the mean of these runs. See example 7 for details.

A basic nutrient feed concentrate consisting of glucose, phosphate, glutamine and the 15 other amino acids was prepared based on the nutrient utilization profile of six duplicate batch cultures of clone 1 in shake-flask (see, e.g., FIG. 3 of the incorporated '245 application). Similar utilization profiles were observed for clone 2, and, hence, it is expected that the feed strategy described below for clone 1 will also improve yields from other clones, thereby providing a more generic strategy for fed-batch or fed-perfusion cultures of E1-immortalized cells, preferably, retina cells, preferably, cells derived from PER.C6 cells. The concentrate is listed in Table 1. Optionally, calcium and three recombinant growth factors, LongR3 IGF-1, Long EGF and insulin were also added to the feed. At this point, the addition of calcium and the growth factors did not significantly influence the results that were obtained. Glycine appeared not essential for the feed, and was no longer added in later experiments. Insulin was purchased from Sigma, LongR3 IGF-1 and Long EGF were purchased from GroPep. All amino acids were purchased from Sigma. The timing and frequency of addition of the feed concentrates was varied. The time of the first addition was tested at 0, 1, and 2 days prior to nutrient exhaustion. Glucose and phosphate were used as indicators for the start of the feed. A series of bolus additions were made every two days, based on the predicted viable cell concentration. Usually, six feeds were provided. The concentrations of the added components as presented in Table 1 do not take into account the remaining component in the spent medium before the addition (i.e., the concentration of a component after addition into the culture medium will be higher than that provided in Table 1, because before the addition the culture medium will still contain some of this component, as additions, according to the invention, are done before the component is completely used up by the cells).

Figure 4:
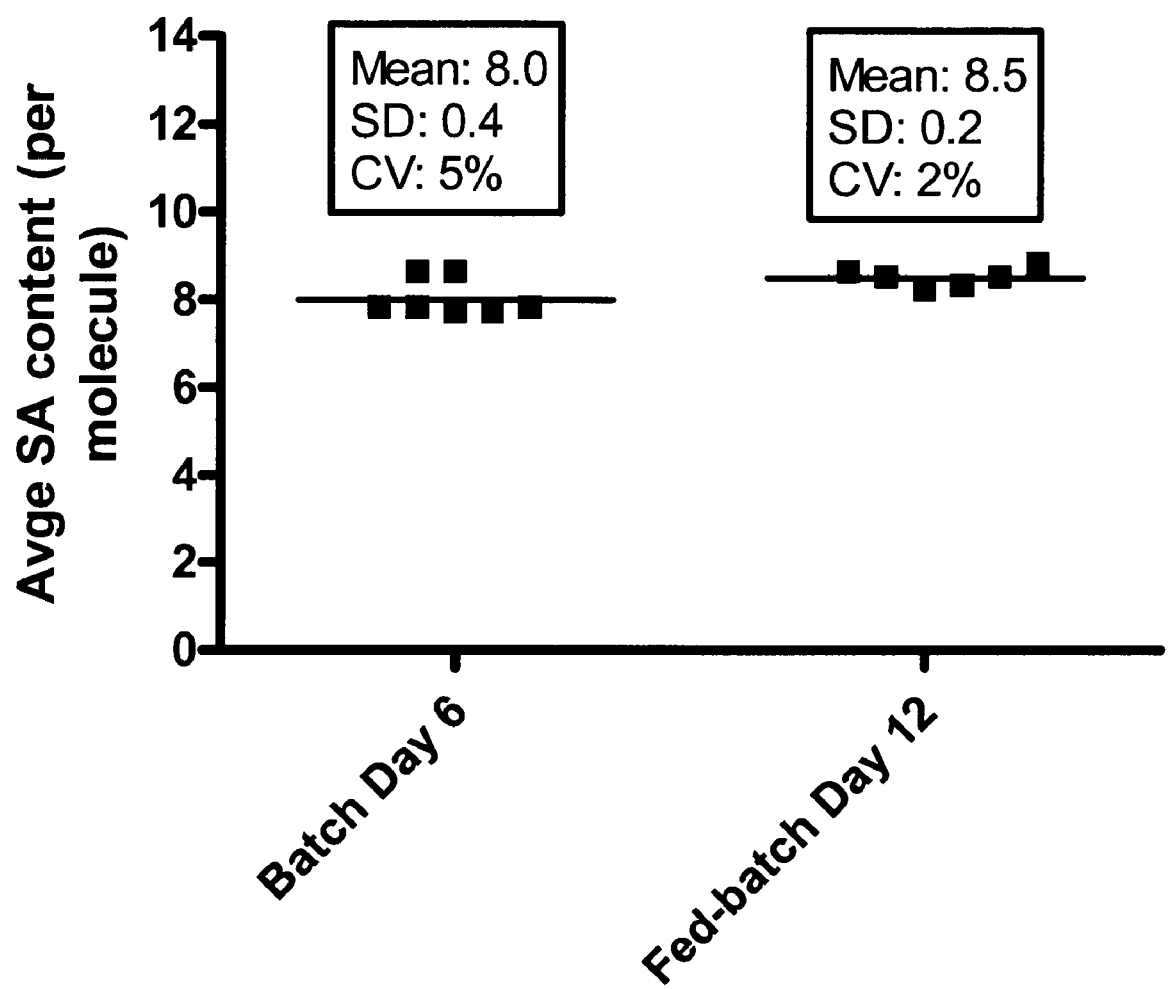
FIG. 4. Average sialic acid content per EPO molecule obtained in several runs of a batch process at day 6 and of a fed-batch process according to the invention at day 12. Dots indicate data points of separate runs, the line represents the mean of these runs. See example 7 for details.

FIG. 4 of the incorporated '245 application shows the effect of feeding the concentrate mix to a sub-clone of PER.C6 expressing a recombinant antibody (clone 1). Starting the feed at day 3 (two days prior to nutrient exhaustion and continuing every two days after this) resulted in a final antibody yield of approximately 800 mg $L^{-1}$, an increase of approximately 1.6-fold over the batch process, which gave 500 mg $L^{-1}$. Starting the feed at day 5 and continuing every two days after this) resulted in a similar increase in final antibody concentration.

Osmolality in the batch cultures (Example 1) decreased from 280 to 240 mOsm $Kg^{-1}$, while in the feed cultures, it increased, eventually rising to 300-310 mOsm $Kg^{-1}$.

Example 3

Achieving Viable Cell Numbers Above $30 \times 10^6$ Cells per ml and Antibody Yields Above 500 mg $L^{-1}$ $Day^{-1}$ Fed-batch processes may result in a build-up of toxic metabolites such as lactate and ammonia and an increase in medium osmolarity, which eventually limit the viable cell concentration and the length of the process, thus, impacting on product yields. A possible alternative to a fed-batch process is a perfusion process, where high cell concentrations can be maintained by a continual medium exchange and a cell bleed (removing a certain percentage of the cells population). A possible drawback with such a process is a relatively low product concentration due to the large volumes of medium that are required, the relatively low cell viability often encountered and the relatively high level of complexity to operate such a system. It is, therefore, only advantageous to operate perfusion processes if very high viable cell concentrations and/or specific productivities can be maintained.

We present here the attainment of a viable cell concentration above $30 \times 10^6$ $ml^{-1}$ and antibody yields of above 600 mg $L^{-1}$ 24 $hours^{-1}$ in shake flask cultures with one medium volume exchange per day.

Logarithmic cultures of antibody producing PER.C6 cells, cultured in shake flask with EXCELL™ 525 were transferred into shake flasks containing EXCELL™ VPRO at a starting cell number $1 \times 10^6$ cells/ml (other starting cell concentrations gave similar results). Medium replacement by centrifugation (one volume per day) was started at day 3-5. No cell bleed was operated. Samples for metabolite analysis, antibody quantification, and cell counts were taken every day and stored at −20° C.

FIG. 5 of the incorporated '245 application shows that a viable cell number of up to $50 \times 10^6$ $ml^{-1}$ and an antibody yield of 500-750 mg $L^{-1}$ 24 $hours^{-1}$ was maintained for at least five days without a cell bleed, for two independent antibody producing cell clones. Viability of the cells was around 80-90%. These high cell densities are approximately three-fold higher than is generally achievable with other cell lines like CHO and Sp2/0, and, hence, retina cells that are immortalized with adenovirus E1 sequences, such as PER.C6 cells, are very suitable for perfusion processes. A cell bleed will improve the length of the process, and, therefore, an optimized system may include one or more cell bleed steps.

Up to $50 \times 10^6$ cells per ml, with a viability of around 80-90%, could be maintained for at least five days with one complete medium change every two days. With this strategy, many of the nutrients became depleted on the second day. The medium is therefore, preferably, changed daily. In a perfusion process, this could translate into a change of about 1 to 3 volumes/day. This is near the typical range in a standard perfusion system, where the medium is changed at about 0.5 to 2 volumes/day. The somewhat higher values for the cells, according to the invention, are due to the very high cell concentrations with the cells of the invention in a perfusion system. When cell concentrations of more than $30 \times 10^6$ cells/ml according to the invention are preferred, the medium exchange should at least be 0.5 culture volumes/day, preferably, at least one culture volume/day. Failure to supply the nutrients (here via the culture medium) in sufficient concentration leads to cell death. The daily medium change results in higher viable cell densities (up to $50 \times 10^6$ cells/ml with daily medium change vs. $10 \times 10^6$ cells/ml without daily medium change, see FIGS. 1 and 4 of the incorporated '245 application). Furthermore, with a daily medium exchange, the cells give similar product yields in one day as achieved in a batch process of 8 to 13 days.

Example 4

Feed Strategies for Further Improving Antibody Yields in PER.C6 Derived Sub-Clones The provision of a balanced nutrient feed extends to components such as vitamins, trace elements and lipids. Concentrates (10× or 50×, both worked) of EXCELL® VPRO vitamins, inorganic salts, trace elements, growth factors, lipids and plant hydrolysates were obtained from JRH Biosciences and added together with the basic feed concentrate (minus calcium and growth factors) described in Example 2. The EXCELL® VPRO concentrates were added to give a final concentration of 0.25×.

FIG. 6 of the incorporated '245 application shows the results of this modified feed on the growth (FIG. 6A) and antibody yields (FIG. 6B) of clone 1 in shake-flask versus a batch control. The results were obtained by starting the feed at day 3 (48 hours prior to nutrient depletion). Starting the feed at day 5 (day of nutrient depletion) gave similar results. The viable cell number was maintained for significantly longer than the batch control and antibody yields increased 2.0-fold from 0.5 g $L^{-1}$ in the batch to 1.0 g $L^{-1}$ in the fed-batch process.

Spent medium analysis of these feed experiments identified a change in the cell specific rates of utilization of some of the amino acids, which appeared to be due to the addition of the VPRO concentrates. The amino acid concentrate listed in Example 2 was, therefore, modified as shown in Table 2. The feed was started 48 hours prior to nutrient depletion and additions were made every two days. Usually, six feeds were provided. Again, the concentrations of the added components as presented in Table 2 do not take into account the remaining component in the spent medium before the addition.

For the first feed addition, increased concentrations of glutamine and serine were used as compared to the subsequent feeds (see Table 2). Phosphate and glucose were used as markers to determine the start of the feed. Clones 1 and 2 were used in this experiment.

Experiments were carried out in shake-flask and bioreactor. Shake flask experiments were carried out as described. Bioreactor experiments were initiated by inoculating a 3L bioreactor (Applikon, 2L working volume) with cells from a logarithmic pre-culture grown in shake flask. The pre-culture and bioreactor experiments were performed in EXCELL® VPRO. The split ratio for inoculation into the bioreactor was at least 1:6, and the seeding cell concentration was about $0.3 \times 10^6$ cells/ml.

Results

FIG. 7 of the incorporated '245 application shows the results of the modified feed on clone 1 in bioreactor versus a batch control. The maximum viable cell number reached 10-12×$10^6$ $ml^{-1}$ and viable cell numbers were maintained between 8 and 10×$10^6$ cells $ml^{-1}$ until the end of the culture at day 19 (FIG. 7A of the incorporated '245 application). Antibody yields increased three-fold from 0.4 g $L^{-1}$ in the batch to 1.3 g $L^{-1}$ in the fed-batch process (FIG. 7B of the incorporated '245 application).

Osmolality and ammonia reached 430 mOsm $Kg^{-1}$ and 16 mmoles $L^{-1}$, respectively, in these feed cultures, levels that have been reported as having negative effects on culture performance and product quality. It may, therefore, be that the decrease in viable cell numbers observed towards the end of the process was due, at least in part, to these factors.

FIG. 8 of the incorporated '245 application shows the results of the feed strategy on clone 2 in 2L bioreactors. Maximum viable cell numbers reached 10-11×$10^6$ $ml^{-1}$ and 7-9×$10^6$ $ml^{-1}$ were maintained until the end of the culture at 19 days. Antibody yields were increased three-fold from 0.5 g $L^{-1}$ to 1.5 g $L^{-1}$.

A third clone expressing another, again unrelated, antibody was subjected to the same batch process and the fed-batch process with the same feed strategy. FIG. 10 of the incorporated '245 application shows the results of the feed strategy on this clone 3 in shake flask. Maximum viable cell numbers reached 14×$10^6$ $ml^{-1}$ and 10-12×$10^6$ $ml^{-1}$ were maintained until the end of the culture on day 17. Antibody yields were increased three-fold from 0.7 g $L^{-1}$ to 2.1 g $L^{-1}$.

The feed strategy, therefore, improves the yield for different clones that each express a different antibody, indicating that the process, according to the invention, is generically applicable.

It is, therefore, an aspect of the invention to provide a process comprising the feed strategy, according to the invention, wherein the yield of a produced protein is increased at least 1.5×, preferably, at least 2×, more preferably, at least 2.5×, still more preferably, at least 3× over the yield in the batch process.

The specific productivity ($q_{Ab}$) of the cells used in the present invention was approximately between 12 to 18 pg antibody/cell/day. In some instances the $q_{Ab}$ was around 10 pg antibody/cell/day, and in other instances values up to about 25 pg antibody/cell/day were observed with the cells and methods of the present invention. In the batch cultures, this decreased significantly before maximum cell numbers were reached, coinciding with depletion of nutrients, which was approximately after seven days, whereas in fed-batch cultures this specific productivity was kept at this level until two to three days after the last feed addition, which amounted to around 16 to 18 days, according to a process of the invention.

Product Quality

In the experiments described above, product quality was checked by various methods, including iso-electric focusing, SDS-PAGE, MALDI-TOF mass spectrometry and HPAEC-PAD. In all cases, the produced antibody basically showed a human-type glycosylation and the structural integrity of the produced antibodies was very good, irrespective of the process used, and very similar to that reported in (Jones et al., 2003), where both cell numbers and product yields were lower. Therefore, the increased yields obtainable by processes of the invention were not obtained at the cost of a significant decrease in product quality.

Protein A purified IgG produced from batch and fed-batch cultures was analyzed by MALDI-MS. Material produced by PER.C6 cells from batch cultures showed a galactosylation profile similar to that shown by IgG purified from human serum and no hybrid or high mannose structures were identified in either batch or fed-batch produced material. The average percentage of glycans terminating in 0, 1, and 2 galactose residues (G0:G1:G2) from all the batch cultures tested was 29, 54, and 17%, respectively. This can be compared to CHO and hybridoma produced antibody, which is often predominantly in the G0 form. For example, Hills et al. (1999) reported a galactosylation profile (G0:G1:G2) for an antibody produced in NSO and CHO cells.

Antibody produced in the fed-batch process showed a reduced level of galactosylation compared to the batch (FIG. 9 of the incorporated '245 application). The percentage of G0 glycoforms increased from 29 to 49%, while the G1 and G2 glycoforms decreased from 54% and 17% to 42% and 9%, respectively. This decrease in galactosylation was probably due to the high (up to 16 mM) ammonia concentrations at the end of the fed-batch cultures. However, the level of galactosylation in the antibody produced by the fed-batch process in PER.C6 cells was still higher than typically seen in batch-produced antibodies from CHO, for example, (Hills et al., 1999). Isoelectric focusing (IEF) and SDS-PAGE revealed no significant differences between the material produced by batch or fed-batch cultures (data not shown) and in all cases, aggregation was below 3%.

Despite relatively low $Y_{amm/gln}$ values, the high viable cell concentrations resulted in a supply of glutamine in the feed such that the ammonia accumulated up to 16 mmoles $L^{-1}$. While this did not result in a drop in the viable cell concentration, batch cultures initiated in the presence of $NH_4Cl$ showed that concentrations above 9 mmole $L^{-1}$ negatively affected growth rates and maximum cell concentrations. Furthermore, glycosylation was also somewhat affected (see FIG. 9 of the incorporated '245 application). It may, therefore, be beneficial to reduce ammonia accumulation, e.g., according to a method described below.

Two areas for attention in the process described so far are the high levels of ammonia and osmolality. A large contributor to the increase in osmolality came from the VPRO (medium) concentrates. An approach to reduce this osmolality is, therefore, to identify which of the medium component groups (vitamins, trace elements, inorganic salts, growth factors etc.) are important to culture performance and remove those that are not important. This should benefit the process, not only by reducing the osmolality of the feed, but also by removing any potentially deleterious components and by allowing the optimization of addition of the most important components. It would also reduce the cost of the feed.

Reduction in ammonia accumulation may be achieved by more strictly controlling glutamine addition. This can be done based on the calculations of the specific consumption and cell numbers, as described supra. This can be achieved by continuously pumping in glutamine at an appropriate rate, matched to the viable cell concentration and the cell specific rate of utilization, so that residual glutamine concentrations in the medium are maintained at a constant low level, such as between 0.2 and 1.5 mM, preferably, between 0.5 and 1.0 mM. Another approach that may be possible for the cells, according to the invention, is the removal of glutamine from the feed when the ammonia concentration reaches a certain point, e.g., in one or more of the feeds, subsequent to the first feed, so that the cells are forced to switch to glutamine synthesis using ammonia and glutamate and the glutamine synthetase pathway. This approach is not generally possible for cell types such as BHK and CHO, as glutamine depletion often results in rapid and widespread cell death and transfer to glutamine-free conditions often requires a period of adaptation. However, in batch cultures of the cells, according to the present invention, the viable cell concentration continued to increase for two days after the depletion of glutamine and culture viability was not significantly affected, suggesting that there may be sufficient flux through the glutamine synthetase pathway at least to maintain the culture.

Spent medium analysis of the most optimized fed-batch culture (examples in FIGS. 7, 8 of the incorporated '245 application) showed that only cystine was depleted during the process. A further modification of the amino acid feed, according to the invention, is, therefore, an increase in the cystine concentration, e.g., to 0.3 to 0.35 mmoles/l or even up to 0.6 mmoles/l for every $10 \times 10^6$ cells/ml.

Example 5

Improved (Fed-)Batch Process

Feed concentrates developed for fed-batch processes may also be used to supplement culture media for use in an improved batch process. Supplementing a culture medium with at least one of the feed additions from a fed-batch process has been shown by others to improve batch yields. A similar approach of supplementing culture media with feed concentrates may also be used to reduce the number of feed additions during a fed-batch process, thereby simplifying the process, as also shown by others.

The present invention discloses feed strategies for cells that have been immortalized by adenovirus E1 sequences, such as PER.C6 cells. It is shown herein which components become limiting in a fed-batch process, and the amounts of, as well as the ratio between, the components that can be added to improve yields in a fed-batch process are disclosed herein. This information is used, in this example, to provide an improved batch process. It is assumed that such a culture will contain about $10 \times 10^6$ cells/ml, as this is around the number of cells that has been observed in the batch and fed-batch cultures of the invention. In the fed-batch experiments, six feeds were added, with concentrations of the components as in Tables 1 or 2. The addition of 10% to 60% of the total (i.e., the total of all six feeds together) feed, preferably, 20% to 40% of the total feed, results in an improved batch process, because the nutrients will become depleted later during the culture, and, hence, the yields will go up because of prolonged productivity compared to the straight batch process disclosed above, where no additions are made to the culture medium. The components can be added directly to the culture medium at any stage prior to depletion of nutrients from the medium, but are, preferably, added prior to start of the culture so that no other additions have to be made during the process (improved batch process), which makes the process very simple. Of course, this may be combined with extra additions of certain components later during the process (fed-batch process), in which case less additions have to be made to make the process than in the fed-batch process disclosed above, thereby providing a simpler fed-batch process. It is, therefore, another embodiment of the invention to provide a method for producing a product in cells immortalized by adenovirus E1 sequences, wherein the cells are cultured in a culture medium, characterized in that the following components are added to the culture medium in the following amounts: glucose (3.6-21.6 mmoles/l, preferably, 7.2-14.4 mmoles/l), glutamine (6.8-40.9 mmoles/l, preferably, 13.6-27.2 mmoles/l), leucine (0.40-2.4 mmoles/l, preferably, 0.79-1.6 mmoles/l), serine (2.31-13.9 mmoles/l, preferably, 4.62-9.24 mmoles/l), isoleucine (0.3-1.8 mmoles/l, preferably, 0.6-1.2 mmoles/l), arginine (0.28-1.66 mmoles/l, preferably, 0.55-1.10 mmoles/l), methionine (0.14-0.83 mmoles/l, preferably, 0.28-0.55 mmoles/l), cystine (0.15-0.9 mmoles/l, preferably, 0.3-0.6 mmoles/l), valine (0.27-1.62 mmoles/l, preferably, 0.54-1.08 mmoles/l), lysine (0.26-1.58 mmoles/l, preferably, 0.53-1.06 mmoles/l), threonine (0.18-1.08 mmoles/l, preferably, 0.36-0.72 mmoles/l), asparagine (0.06-0.36 mmoles/l, preferably, 0.12-0.24 mmoles/l), tyrosine (0.078-0.47 mmoles/l, preferably, 0.16-0.31 mmoles/l), histidine (0.06-0.36 mmoles/l, preferably, 0.12-0.24 mmoles/l), phenylalanine (0.012-0.072 mmoles/l, preferably, 0.024-0.048 mmoles/l), tryptophan (0.036-0.22 mmoles/l, preferably, 0.072-0.14 mmoles/1) and phosphate (0.45-2.7 mmoles/l, preferably, 0.9-1.8 mmoles/l). The amounts between brackets are 10% to 60%, preferably, 20% to 40%, of the amounts of 6× the feeds of Table 2. Preferably, also culture medium concentrate (10×, 50×, or other suitable concentrates can be used) is added to an end concentration of between 0.15×-0.9×, preferably, between 0.3×-0.6×. Preferably, the culture medium in these embodiments is ExCell VPRO medium. An amount of 0.5, 1, 1.5, 2, 2.5, 3, 3.5 or 4 single feeds (a single feed being an amount as disclosed in Table 1 or 2) is added to culture medium, and simple batch processes for culturing the cells at around $10 \times 10^6$ cells/ml and producing product (e.g., antibody), according to the invention, are performed with the, thus, fortified media, to determine the optimum amount of component additions. Improved batch processes giving the highest product yields are expected when about 20% to 40% of the total feed of a fed-batch process, according to the invention, are provided to the culture medium prior to culturing somewhere between 1 to 2.5 single feeds. Of course, more fine-tuning of the amount is possible once a beneficial range of added components is established by these experiments. Of course, when the cell numbers are different, the component addition can again be adapted. For instance, if the cells are cultured at a density of only 5×10⁶ cells/ml, addition of an amount of only half the amount above would be required, as is clear to the person skilled in the art.

Example 6

Fed-batch Process Used for Yet Other Antibody Clones

Other cell culture media have been tested instead of Excell® VPRO medium, e.g. HyQ® CDM4Retino™ supplemented with either 1 or 10 mM galactose, and exactly the same feed as described in example 4 was used for production of recombinant antibodies in PER.C6 cells, with similar results (data not shown). The 10 mM galactose in this medium gave better results than 1 mM galactose, which in turn gave better results than no addition of galactose. Overall these experiments show that the feed strategy as described herein is generally applicable for PER.C6 cells and can be used for a fed-batch process in other culture media as well.

Batch and fed batch experiments were performed with two cell lines expressing another monoclonal antibody (clone 4a and 4b). The feed strategy was the same as described in example 4 using 50× concentrates of EXCELL® VPRO (50× inorganic salts, trace elements, vitamins, growth factors, lipids and plant hydrolysate) obtained from JRH Biosciences and added together with the basic feed concentrate (minus calcium and growth factors). The total feed composition is shown in Table 3. The EXCELL® VPRO concentrates were added to give a final concentration of 0.25×.

FIGS. 1 and 2 show the results of the feed strategy on these two cell lines in shake flask. Maximum viable cell numbers reached $16 \times 10^6$ ml$^{-1}$ and $10 \times 10^6$ ml$^{-1}$ for clone 4a and 4b respectively. Antibody yields in the fed-batch were increased approximately four-fold compared to batch yields for both cell lines, from $0.9$ g L$^{-1}$ to $3.5$ g L$^{-1}$ for clone 4a and from $0.8$ g L$^{-1}$ to $3.0$ g L$^{-1}$ for clone 4b. The specific productivity of clone 4a and 4b was approximately 22 and 31 pg cell$^{-1}$ day$^{-1}$ respectively.

Example 7

Production of EPO in Batch and Fed-Batch Cultures

The methods used for purification, quantification and analysis of EPO as used are described first, because these are the same for the following examples.

Purification of EPO from PER.C6 Cell Culture Supernatants

Samples were purified using affinity chromatography with an anti-human EPO antibody (E14) coupled to CNBr-activated sepharose. Briefly, the method uses 1 ml of 50% E14 antibody coupled to Sepharose in a 50 ml centrifuge tube for each sample. The sepharose-coupled antibody was first washed with 50 ml PBS, pH 7.4 for 5 minutes. The sample was then applied to the E14 coupled-sepharose and incubated for 60 minutes. The supernatant was then removed by centrifugation at 3000 rpm for 2 minutes and the sepharose washed with 50 ml PBS, pH 7.4 for 5 minutes. A second wash using 0.1 M NaCl was performed. Two elution steps were performed each using 2 ml of 0.1 M glycine, pH 2.7 with gentle mixing for 10 minutes. The material from each elution was neutralized by adding 550 ul of 1M TRIS, mixed, sterile filtered and stored at 4° C.

EPO Quantification

Concentration of erythropoietin was measured using a commercially available ELISA (Quantikine® IVD® Erythropoietin ELISA, R&D Systems Inc., Catalog number DEP00). It is noted that 1 eU in this assay in general corresponds to about 5-10 ng EPO, depending on the sialic acid content of the EPO, wherein EPO with a higher sialic acid content in general corresponding to a higher concentration of EPO per eU. As an example, for commercially available EPREX 1 eU corresponds to 8.4 ng EPO. For the molecules obtained by the processes of the invention with a sialic acid content of between about 8 and 10, 1 eU typically corresponds to about 6-8 ng EPO. Hence, for example a value of 5000 eU/ml in the experiments below, corresponds to about 30-40 mg/l.

Determination of Sialic Acid Content of EPO

The sialic acid content of various samples of affinity purified, PER.C6-produced EPO was analyzed as described in example 50 of US 2005/0181359. In particular, this was done using iso-electric focusing, which was performed on an Iso-Gel agarose IEF plate (Cambrex) soaked in an ampholyte solution pH 3-10 containing 8 M urea. Other IEF plates or gels, also with a pH range of pH 3-7, have been used with similar results. The EPO bands were visualized with colloidal blue (Novex). The bands represent EPO isoforms containing different numbers of sialic acids per EPO molecule. The relative amount for each isoform was determined using densitometric analysis of the bands. The average number of sialic acid residues per EPO molecule was calculated using the formula:

$$\sum_{n=0-15} (A_n * n)$$

A=relative amount of each isoform
n=isoform number (corresponding to the number of sialic acid residues per EPO molecule)

Using this method, the average sialic acid content of EPREX® (a commercially available EPO preparation) was 12.4.

Alternative methods to calculate the sialic acid content of the recombinant EPO fractions could also be used, e.g. the method described in U.S. Pat. No. 5,856,298, example 2, or a procedure described in example 5 of CA 2309810 A1, or a procedure as described by Jourdian et al, J Biol Chem. 246, 430 (1971), or modifications of such methods known to the person skilled in the art.

Cell Line

A PER.C6 cell line expressing human Erythropoietin and co-expressing rat α2,6-sialyltransferase (PER.C6-EPO-ST clone 25-3.10) was used in this experiment. The generation of this cell line was described previously (see e.g. example 36 of US2005/0164386).

Cell Culture

Cell cultures were maintained in HyQ® CDM4Retino™, a chemically defined serum free medium (HyClone, Catalog number SH30520). Cell cultures were passaged every 2-4 days by performing a complete medium change. Spent medium was removed by centrifugation at 1000 rpm for 3-5 minutes and the cell pellet re-suspended in fresh medium at a seeding cell concentration of 0.2-0.4×10⁶ viable cells per ml. Cells were cultured in 250 ml Ehrlenmeyer shake flasks (Corning) on shaker platforms (Orbitec, Infors) at 100 rpm and in a humidified incubator at 37° C. and 5% CO2.

Batch and Fed-Batch

Batch and fed-batch cultures were initiated from logarithmically growing pre-cultures in 250 ml shake flasks containing 30 ml of CDM4Retino supplemented with 10 mM galactose. Cells were seeded at $0.3\times10^6$ viable cells per ml and incubated as described above for the pre-cultures. Samples (approx. 0.5-1 ml) were taken as indicated and used to determine cell counts (CASY TT, Schaerfe Systems) and EPO concentration. Batch cultures were harvested on day 6, fed-batch cultures on day 12 and the samples purified by affinity chromatography and then analysed by Isoelectric focusing (IEF) to determine the average sialic acid number.

Fed-batch cultures were performed using the same generic PER.C6 feed concentrate and feed strategy as described above (see examples 4 and 6).

Batch culture yields reached an average of 858 eU per ml on day 6 (FIG. 3), and the purified EPO from these harvests contained an average sialic acid number of 8.0 (FIG. 4). Fed-batch yields reached an average of 5605 eU per ml on day 12 (FIG. 3), a 6.5-fold increase over the batch yield. The average sialic acid content of the purified EPO from these harvests was 8.5 (FIG. 4).

Hence, the 12-day fed-batch culture significantly improved the yield of EPO product obtained, while at the same time the quality of the EPO as indicated by the average sialic acid content did not decrease. Therefore, the fed-batch culture method is very suitable to obtain high expression levels of recombinant EPO with a high average sialic acid content from human embryonic retina cells that also express adenoviral E1A sequences and that further contain a sialyltransferase under control of a heterologous promoter.

Example 8

Production of EPO in Batch and Fed-Batch Cultures Using a Cell Line Engineered with an α-2,3-sialyltransferase Cell Lines PER.C6 cell lines expressing human Erythropoietin and co-expressing human α2,3-sialyltransferase was used for these studies. These cells were generated as described in example 53 of US 2005/0181359, incorporated by reference herein. Briefly, PER.C6 cells were transfected with plasmid pEPO-ST3 (a plasmid for co-expression of EPO and human α-2,3-sialyltransferase, see example 51 of US 2005/0181359, incorporated by reference herein). Clones were obtained and clones for further analysis were chosen based on yield and sialic acid content of EPO produced in serum-containing medium. Selected clones were used for production in serum-free medium as described below. One clone (PER.C6-EPO-ST clone 078, further referred to as clone 078) was used for the most extensive analysis and is used for further experiments.

Cell Cultures

Cell cultures were maintained in Mab medium, a serum free medium (JRH Bioscience). Cell cultures were passaged every 2-3 days by performing a complete medium change. Spent medium was removed by centrifugation at 1000 rpm for 3-5 minutes and the cell pellet re-suspended in fresh medium at a seeding cell concentration of $0.2-0.4\times10^6$ viable cells per ml. Cells were cultured in 250 ml Ehrlenmeyer shake flasks (Corning) on shaker platforms (Orbitec, Infors) at 100 rpm and in a humidified incubator at 37° C. and 5% $CO_2$.

Batch and Fed-batch Cultures

Batch cultures were initiated from logarithmically growing pre-cultures in 250 ml shake flasks containing 30 ml of ExCell® VPRO (JRH Bioscience). Cells were seeded at $0.3\times10^6$ viable cells per ml and incubated as described above for the pre-cultures. Samples (approx. 0.5-1 ml) were taken as indicated and used to determine cell counts (CASY TT, Schaerfe Systems) and EPO concentration as described above (see example 7). Batch cultures were harvested on day 7 and the samples purified by affinity chromatography and then analysed by Isoelectric focusing (IEF) to determine the average sialic acid number, as described above (see example 7).

Apart from clone 078, EPO yields produced by three similar cell lines expressing human Erythropoietin and co-expressing human α2,3-sialyltransferase in 7-day batch cultures ranged from 1698 eU/ml to 8319 eU/ml while the average sialic acid content ranged from 8.5 to 9.9 (data not shown). One clone, clone 078, was used for further analysis based on the yield and sialic acid content of EPO produced by this clone.

FIG. 5 shows that the average EPO yields obtained from this clone 078 was 7669 eU/ml with an average sialic acid content of 10.0.

EPO produced in these batch cultures was purified by affinity chromatography and then quantified by reversed phase high-pressure liquid chromatography (RP-HPLC). The concentration of EPO after the affinity purification step was found to be approximately 56-58 mg $L^{-1}$.

Fed batch cultures are performed with clone 078 in ExCell® VPRO (JRH Bioscience) and in HyQ CDM4Retino (Hyclone) supplemented with galactose, as described in example 7. It is expected that the yield will improve over those obtained for the batch process while the average sialic acid content will remain in the same range.

Example 9

Obtaining EPO with Further Increased Average Sialic Acid Content

It is shown above (examples 7 and 8) that EPO with high sialic acid content can be obtained in the batch or fed-batch processes described (average sialic acid contents of about 8-10). Since a high sialic acid content for EPO in general is beneficial for in vivo biological activity, it may be useful to further fractionate the material obtained by the (fed)-batch processes to obtain EPO with an average sialic acid content that is still higher, e.g. between about 12-15. This example describes methods to obtain fractions of EPO with such sialic acid contents using cells and processes according to the invention.

In this example, EPO was recombinantly produced in stably transfected PER.C6 cells over-expressing a sialyltransferase (either α-2,6-sialyltransferase or α-2,3-sialyltransferase, see examples above; such cells are referred to as PER.C6-ST cells) in serum-free suspension cultures, using batch processes. The EPO preparations produced are referred to as 2,6 EPO and 2,3 EPO, respectively.

Preculture: Ampoules containing cryopreserved PER.C6-ST cells producing EPO, were thawed into Erlenmeyer shake flasks containing Mab medium. Shake flask cultures were maintained in a humidified incubator on orbital shake plateaus (37° C., 5% $CO_2$, 100 RPM). Every 2-3 days, cells were subcultured with a complete medium exchange by centrifugation. The target seeding density of each passage was $0.2-0.3*10^6$ viable cells/mL.

Preparation of inoculum for the productions in a batch process: To prepare inoculum, the last preculture passage was performed in VPRO medium. PER.C6-ST cells expressing EPO precultured in Mab medium were subcultured by centrifugation, and a complete medium exchange to VPRO medium was performed. The target seeding cell density was $0.4-0.6*10^6$ viable cells/mL, and shake flask cultures were maintained in a humidified incubator on orbital shake plateaus (37° C., 5% $CO_2$, 100 RPM). After 3-4 days of incubation, the cultures were used as inoculum for the batch productions.

Alternatively, the inoculum was prepared in Mab medium. In this case, the cells precultured in Mab medium were subcultured by centrifugation, and seeded at a target cell density of $0.2$-$0.3*10^6$ viable cells/mL in shake flasks or in bioreactors, containing Mab medium. Shake flask cultures were maintained in a humidified incubator on orbital shake plateaus (37° C., 5% $CO_2$, 100 RPM). Bioreactor settings were as follows: temperature was maintained at 37° C., dissolved oxygen concentration ($dO_2$) was controlled at 50% of air saturation by $O_2$ sparging and culture pH at inoculation was controlled below 7.3 by $CO_2$ addition in the headspace. No low limit pH control was operated. After 2-3 days of incubation, the cultures were used as inoculum for the batch productions.

Production in batch process: Batch cultures in VPRO medium were initiated by diluting the inoculum prepared in VPRO medium into fresh VPRO medium, or by a complete medium exchange to VPRO medium by centrifugation in case the inoculum had been prepared in Mab medium. Batch cultures were started at a target seeding density of $0.2$-$0.4*10^6$ viable cells/mL in shake flasks or bioreactors. Shake flask cultures were maintained in a humidified incubator on orbital shake plateaus (37° C., 5% $CO_2$, 100 RPM). Bioreactor settings were as follows: temperature was maintained at 37° C., dissolved oxygen concentration ($dO_2$) was controlled at 50% of air saturation by $O_2$ sparging and culture pH at inoculation was controlled below 7.3 by $CO_2$ addition in the headspace. No low limit pH control was operated.

Harvest: Cultures of PER.C6-ST cells expressing EPO were harvested at one day after the maximum viable cell density had been reached; typically between 5-9 days after initiation of the batch cultures. EPO concentrations as determined by ELISA ranged approximately from 1000 to 10000 ELISA Units/mL, dependent on the cell line, the specific clone, and the culture format.

Cells were removed from the crude batch harvest by means of centrifugation at 300 g for 5 minutes (Heraeus, Multifuge), followed by clarification over a disposable coarse clarification filter (Millipore, Clarigard Opticap XL, 3 μm) and a disposable fine filter (Sartorius, Sartopore 2, 0.8/0.45 μm).

Purification and anion exchange: EPO was purified from the filtrated batches on a 90 ml CV mouse monoclonal anti-EPO (IgG1) bound to CNBr-activated Sepharose 4B (Amersham Biotech) column with a flow rate of 5 ml/min (see example 7 above). Elution and fractionation by anion exchange was done as described in example 48 of US 2005/0181359, incorporated by reference. All fractionated and non-fractionated materials were transferred to Standard Storage Buffer (0.03% Tween 80, 0.5% Glycine in PBS pH7.4) by means of buffer exchange with a size exclusion column (HiPrep 26/10). After Buffer Exchange the samples were sterile filtered over a 0.2 μm filter (Pall, Acrodisc PN4908).

Source 15Q fractionation: Affinity-purified material was buffer exchanged using a Hiprep 26/10 desalting column (GE Healthcare) to 20 mM Tris/20 μM $CuSO_4$ pH 8.0. After loading the Source 15Q column (Amersham) was washed with 20 mM Tris/20 μM $CuSO_4$ 50 mM NaCl pH 6.0, followed by elution with increasing amounts of (1M) NaCl in 20 mM Tris/20 μM CuSO4 pH 6.0. Step gradients of 5-15%, 15-25%, 25-30%, 30-50%, and 50-100% were used. Fractions eluting at 250-300 mM NaCl were pooled. The sialic acid content of the fractions of EPO was analyzed using IEF as described above (see example 7). After analysis fractions were pooled.

The 2,6 EPO thus obtained had an average sialic acid content of 12.1, and the 2,3 EPO thus obtained had an average sialic acid content of 12.7.

It was tested whether fractions with still further increased sialic acid content could be obtained. A novel batch of 2,3 EPO was produced from clone 078 (see example 8) and affinity purified as described above in this example. To enrich for fractions with a higher sialic acid content two alternative preparative iso-electric focusing (IEF) methods were used as described below. Alternatively preparative size exclusion chromatography (HP-SEC) was used.

Ultrodex purification: Affinity purified material was further separated on a preparative IEF gel in a low pH range (Ultrodex, pH 3-5; Amersham Biosciences) in the presence of 5 M Urea. The sample was separated into isoforms. Isoforms were extracted from the Ultrodex by elution with 0.5 M Tris-HCl pH 8.0. Fractions were pooled and dialysed against PBS. Tween-80 and Glycine were added to respective final concentrations of 0.03% (v/v) and 0.5% (w/v) and the preparation was sterile filtered (0.22 μm Millex-GV filter, Millipore).

Rotofor purification: Alternatively, affinity purified material was further separated by using preparative IEF (Rotofor, Biorad). 2.5-5 mg of purified EPO was loaded in the Rotofor and isoforms were separated in a low pH range, pH 2-4, in 5 M Urea. This resulted in a maximum of 10 fractions with different isoforms. Appropriate fractions were pooled. These pooled fractions were dialysed against PBS. Tween-80 and glycine were added to final concentrations of 0.03% (v/v) and 0.5% (w/v) respectively and the preparation was sterile filtered (0.22 μm Millex-GV filter, Millipore).

The sialic acid content of various fractions of EPO was analyzed using IEF as described above (see example 7) and is shown in Table 4. It is clear that fractions with an average sialic acid content of between about 12 and 15 can thus be obtained from the starting material produced by a batch process using the cells as described.

The in vivo biological activity of EPO as determined by an in vivo bioassay in Normocythaemic mouse according to PHEUR 01/2002:1316, was found to be generally increased with increasing sialic acid content for the fractions that were tested (data not shown). For instance, the EPO preparation thus obtained with a sialic acid content of 14.3 (PER.C6 2,3 EPO-2, approximate yield 3%) had a specific activity of 113.881 IU/mg [95% confidence interval 94836-139361 IU/mg], which is comparable to that of a commercially available Epo preparation tested (Eprex™, which in turn is comparable to the EPO BRP standard both in activity and in sialic acid content). Hence, it is possible to obtain EPO with a similar in vivo biological activity as commercial EPO preparations, using E1A expressing cells that also over-express a sialyltransferase, when EPO is produced in a batch process.

EPO preparations with increased sialic acid content are similarly prepared from material obtained by a fed-batch process according to the invention (e.g. material obtained from a fed-batch process with clone 078, see example 8). It is expected that significantly increased amounts of EPO preparations with an average sialic acid content of somewhere between about 12 and 15 will thus be obtained.

TABLE 1

| Components | Final Concentration (after addition) (per $10 \times 10^6$ cells/ml) (mmoles $L^{-1}$) |
|---|---|
| Glucose | 6.00 |
| Glutamine | 1.75 |

TABLE 1-continued

| Components | Final Concentration (after addition) (per 10 × 10⁶ cells/ml) (mmoles L⁻¹) |
|---|---|
| Leucine | 0.60 |
| Serine | 0.55 |
| Isoleucine | 0.45 |
| Arginine | 0.42 |
| Methionine | 0.23 |
| Cystine | 0.14 |
| Valine | 0.45 |
| Lysine | 0.40 |
| Threonine | 0.33 |
| Glycine | 0.33 |
| Asparagine | 0.15 |
| Tyrosine | 0.14 |
| Histidine | 0.11 |
| Penylalanine | 0.10 |
| Tryptophan | 0.02 |
| Phosphate | 0.70 |
| Calcium | 0.02* |
| LongR3 IGF-1 | 50 ug/L* |
| Long EGF | 50 ug/L* |
| Insulin | 20 ug/L* |

*optionally present

TABLE 2

| Components | Final Concentration (after addition) (per 10 × 10⁶ cells/ml) (mmoles L⁻¹) | |
|---|---|---|
| | First Feed | Subsequent Feeds |
| Glucose | 6.00 | 6.00 |
| Glutamine | 2.60 | 1.75 |
| Leucine | 0.66 | 0.66 |
| Serine | 1.10 | 0.55 |
| Isoleucine | 0.50 | 0.50 |
| Arginine | 0.46 | 0.46 |
| Methionine | 0.23 | 0.23 |
| Cystine | 0.25 | 0.23 |
| Valine | 0.45 | 0.45 |
| Lysine | 0.44 | 0.44 |
| Threonine | 0.30 | 0.30 |
| Asparagine | 0.10 | 0.10 |
| Tyrosine | 0.13 | 0.13 |
| Histidine | 0.10 | 0.10 |
| Penylalanine | 0.02 | 0.02 |
| Tryptophan | 0.06 | 0.06 |
| Phosphate | 0.75 | 0.75 |
| 10X VPRO Concentrate | 0.25X | 0.25X |

TABLE 3

| Components | Final Concentration (after addition) (per 10 × 10⁶ cells/ml) (mmoles L⁻¹) | |
|---|---|---|
| | First Feed | Subsequent Feeds |
| Glucose | 6.00 | 6.00 |
| Glutamine | 2.60 | 1.75 |
| Leucine | 0.66 | 0.66 |
| Serine | 1.10 | 0.55 |
| Isoleucine | 0.50 | 0.50 |
| Arginine | 0.46 | 0.46 |
| Methionine | 0.23 | 0.23 |
| Cystine | 0.25 | 0.23 |
| Valine | 0.45 | 0.45 |
| Lysine | 0.44 | 0.44 |
| Threonine | 0.30 | 0.30 |
| Asparagine | 0.10 | 0.10 |
| Tyrosine | 0.13 | 0.13 |
| Histidine | 0.10 | 0.10 |
| Penylalanine | 0.02 | 0.02 |
| Tryptophan | 0.06 | 0.06 |
| Phosphate | 0.75 | 0.75 |
| 50X VPRO concentrate 1 (Inorganic salts + trace elements) | 0.25X | 0.25X |
| 50X VPRO concentrate 2 (Vitamins, growth factors, lipids) | 0.25X | 0.25X |
| 50X Plant hydrolysate | 0.25X | 0.25X |

TABLE 4

| Sample | Fractionation method | Average SA |
|---|---|---|
| 2.3 EPO-1 | Ultrodex | 13.6 |
| 2.3 EPO-2 | Ultrodex | 14.3 |
| 2.3 EPO-4 | Rotofor | 12.68 |
| 2.3 EPO-5 | HP-SEC | 12.38 |
| 2.3 EPO-6 | Ultrodex | 13.55 |
| 2.3 EPO-7 | Rotofor | 13.00 |
| 2.3 EPO-8 | Rotofor | 14.16 |
| 2.3 EPO-9 | Rotofor | 12.61 |
| 2.3 EPO-10 | Rotofor | 12.22 |

Samples with average SA (sialic acid) content after preparative IEF or HP-SEC (see example 9).

REFERENCES

Andersen D C and Goochee C F (1995). The effect of ammonia on the O-linked glycosylation of granulocyte colony stimulating factor produced by Chinese hamster ovary cells. Biotechnol. Bioeng. 47, p96-105.

Boel E., S. Verlaan, M. J. Poppelier, N. A. Westerdaal, J. A. Van Strijp, and T. Logtenberg (2000). Functional human monoclonal antibodies of all isotypes constructed from phage display library-derived single-chain Fv antibody fragments. J. Immunol. Methods 239:153-66.

Byrd P, Brown K W, Gallimore P H. 1982. Malignant transformation of human embryo retinoblasts by cloned adenovirus 12 DNA. Nature 298: 69-71.

Byrd P J, Grand R J A, Gallimore P H. 1988. Differential transformation of primary human embryo retinal cells by adenovirus E1 regions and combinations of E1A+ras. Oncogene 2: 477-484.

Delorme E, Lorenzini T, Giffin J, Martin F, Jacobsen F, Boone T, Elliot S (1992) Role of glycosylation on the secretion and biological activity of erythropoietin. Biochemistry 31, 9871-9876.

Gallimore, P. H., Grand, R. J. A. and Byrd, P. J. (1986). Transformation of human embryo retinoblasts with simian virus 40, adenovirus and ras oncogenes. AntiCancer Res. 6, p499-508.

Gawlitzek M, Ryll T, Lofgren J and Slikowski M (2000). Ammonium alters N-glycan structures of recombinant TNFR-IgG: Degradative versus biosynthetic mechanisms. Biotechnol. Bioeng. 68, p637-646.

Goldwasser E, Eliason J F, Sikkema D (1975) An assay for erythropoietin in vitro at the milliunit level. Endocrinology 97, 315-23.

Gorman C M, Gies D, McCray G, Huang M (1989) The human cytomegalovirus major immediate early promoter can be trans-activated by adenovirus early proteins. Virology 171, 377-385.

Grabenhorst E, Hoffmann A, Nimtz M, Zettlmeissl G, and Conradt H S (1995) Construction of stable BHK-21 cells coexpressing human secretory glycoproteins and human Gal(β1-4)GlcNAc-R α2,6-sialyltransferase. Eur. J. Biochem. 232:718-725.

Graham F L, Smiley J, Rusell W C and Nairn R (1977) Characteristics of a human cell line transformed by DNA from human adenovirus type 5. J. Virol. 36, 59-74

Grundmann U, Nehrlich C, Rein T, Zettlmeissl G (1990) Complete cDNA sequence encoding human beta-galactoside alpha-2,6-sialyltransferase. Nucleic Acids Res. 18: 667.

Harduin-Lepers A, Vallejo-Ruiz V, Krzewinski-Recchi M A, Samyn-Petit B, Julien S, and Delannoy P (2001) The human sialyltransferase family. Biochimie 83:727-737.

Hills A. E., A. K. Patel, P. N. Boyd and D. C. James (1999). Control of therapeutic antibody glycosylation. In: A. Bernard, B. Griffiths, W. Noe and F. Wurm (eds), *Animal Cell Technology: Products from Cells, Cells as Products*, 255-257. Kluwer Academic Press, Dordrecht, The Netherlands.

Huls G. A., I. A. F. M. Heijnen, M. E. Cuomo, J. C. Koningsberger, L. Wiegman, E. Boel, A-R van der Vuurst-de Vries, S. A. J. Loyson, W. Helfrich, G. P. van Berge Henegouwen, M. van Meijer, J. de Kruif, and T. Logtenberg (1999). A recombinant, fully human monoclonal antibody with anti-tumor activity constructed from phage-displayed antibody fragments. Nat. Biotechnol. 17:276-281.

Jenkins N, Buckberry L, Marc A, Monaco L (1998) Genetic engineering of alpha 2,6-sialyltransferase in recombinant CHO cells. Biochem Soc Trans. 26, S115.

Jones D., N. Kroos, R. Anema, B. Van Montfort, A. Vooys, S. Van Der Kraats, E. Van Der Helm, S. Smits, J. Schouten, K. Brouwer, F. Lagerwerf, P. Van Berkel, D-J Opstelten, T. Logtenberg, and A. Bout (2003). High-level expression of recombinant IgG in the human cell line PER.C6. Biotechnol. Prog. 19:163-168.

Leist M, et al (2004) Derivatives of erythropoietin that are tissue protective but not erythropoietic. Science 305, 239-242.

Olive D M, Al-Mulla W, Simsek M, Zarban S, al-Nakib W (1990) The human cytomegalovirus immediate early enhancer-promoter is responsive to activation by the adenovirus-5 13S E1A gene. Arch Virol. 112, 67-80.

Portner R., A. Bohmann, I. Ludemann and H. Markl (1994). Estimation of specific glucose uptake rates in cultures of hybridoma cells. J. Biotechnol. 34:237-246.

Sauer P. W., J. E. Burky, M. C. Wesson, H. D. Sternard and L. Qu (2000). A high yielding, generic process fed batch cell culture process for production of recombinant antibodies. *Biotechnol. Bioeng.* 67:585-597.

Tanase T., Y. Ikeda, K. Iwama, A. Hashimoto, T. Kataoka, Y. Tokushima and T. Kobayashi (1997). Comparison of micro-filtration hollow fiber bioreactors for mammalian cell culture. *J. Ferm. Ioeng.* 83:499-501.

Weikert S, Papac D, Briggs J, Cowfer D, Tom S, Gawlitzek M, Lofgren J, Mehta S, Chisholm V, Modi N, Eppler S, Carroll K, Chamow S, Peers D, Berman P, Krummen L (1999) Engineering Chinese hamster ovary cells to maximize sialic acid content of recombinant glycoproteins. Nature Biotechnology 17, 1116-1121.

Xie L., W. Pilbrough, C. Metallo, T. Zhong, L. Pikus, J. Leung, Auninš and W. Zhou (2002). Serum-free suspension cultivation of PER.C6® cells and recombinant adenovirus production under different pH conditions. *Biotechnol. and Bioengin.* 80:569-579.

Yamaguchi K, Akai K, Kawanishi G, Ueda M, Masuda S, Sasaki R (1991) Effects of site-directed removal of N-glycosylation sites in human erythropoietin on its production and biological properties. J Biol Chem. 266, 20434-20439.

Weidemann R., A. Ludwig and G. Kretzmer (1994). Low temperature cultivation—A step towards process optimization. *Cytotechnology* 15:111-116.

Wohlpart D., D. Kirwan and J. Gainer (1990). Effects of cell density and glucose and glutamine levels on the respiration rates of hybridoma cells. *Biotechnol. Bioeng.* 36:630-635.

Yallop C. A. and I. Svendsen (2001). The effects of G418 on the growth and metabolism of recombinant mammalian cell lines. *Cytotechnology* 35:101-114.

What is claimed is:

1. A process for recombinant production of erythropoietin (EPO) in a human embryonic retina cell that expresses at least an adenoviral E1A protein, wherein said EPO is produced at a concentration of at least 3000 eU/ml, and wherein said EPO as produced has an average sialic acid content per EPO molecule of at least 7, the process comprising:
    a) providing an immortalized human embryonic retina cell that expresses at least an adenoviral E1A protein, said cell further comprising a nucleic acid encoding a sialyltransferase under control of a heterologous promoter, and said cell further comprising nucleic acid encoding EPO under control of a heterologous promoter;
    b) culturing the cell in a serum-free culture medium in a fed-batch process, wherein at least once during said culturing according to needs of nutrients glucose and at least one medium component selected from the group consisting of glutamine, leucine, serine, isoleucine, arginine, methionine, and cystine are added depending on the requirements of the cells; and
    c) harvesting EPO from the culture medium, wherein the EPO is present in the culture medium at a concentration of at least 3000 eU/ml and wherein said EPO as produced has an average sialic acid content per EPO molecule of at least 7.

2. The process of claim 1, wherein said human embryonic retina cell that expresses at least an adenoviral E1A protein is a cell such as deposited at the ECACC under no. 96022940.

3. The process of claim 1, wherein said EPO is produced at a concentration of at least 4000 eU/ml.

4. The process of claim 1, wherein said EPO is produced at a concentration of at least 5000 eU/ml.

5. The process of claim 1, wherein the sialyltransferase is an α-2,6-sialyltransferase.

6. The process of claim 1, wherein the sialyltransferase is an α-2,3-sialyltransferase.

7. The process of claim 1, wherein said EPO as produced has an average sialic acid content per EPO molecule of at least 8.

8. The process of claim 1, wherein said EPO as produced has an average sialic acid content per EPO molecule of between 8 and 12.

9. The process of claim 1, wherein said at least one carbohydrate comprises glucose and galactose.

10. The process of claim 1, wherein at least one further component is added to the culture medium, wherein the further component comprises one or more of valine, lysine, threonine, glycine, asparagine, tyrosine, histidine, phenylalanine, tryptophan, phosphate, calcium, LongR3 IGF-1, Long EGF and insulin.

11. The process of claim 1, wherein glucose is added to an end concentration of between 4.0 and 8.0 mmoles/l of freshly added glucose per 10×10⁶ cells/ml, leucine is added to an end concentration of between 0.44 and 0.88 mmoles/l of freshly added leucine per 10×10⁶ cells/ml, serine is added to an end concentration of between 0.37 and 1.47 mmoles/l of freshly added serine per 10×10⁶ cells/ml, isoleucine is added to an end concentration of between 0.33 and 0.67 mmoles/l of freshly added isoleucine per 10×10⁶ cells/ml, arginine is added to an end concentration of between 0.31 and 0.61 mmoles/l of freshly added arginine per 10×10⁶ cells/ml, methionine is added to an end concentration of between 0.15 and 0.31 mmoles/l of freshly added methionine per 10×10⁶ cells/ml, and cystine is added to an end concentration of between 0.1 and 0.6 mmoles/l of freshly added cystine per 10×10⁶ cells/ml.

12. The process of claim 11, wherein glutamine is further added to an end concentration of between 1.17 and 3.47 mmoles/l of freshly added glutamine per 10×10⁶ cells/ml.

13. The process of claim 11, wherein the following components are further added to an end concentration in mmoles/l of freshly added component per 10×10⁶ cells/ml of between 0.3 and 0.6 for valine, 0.29 and 0.59 for lysine, 0.2 and 0.4 for threonine.

14. The process of claim 13, wherein the following components are further added to an end concentration in mmoles/l of freshly added component per 10×10⁶ cells/ml of between 0.067 and 0.13 for asparagine, 0.087 and 0.17 for tyrosine, 0.067 and 0.13 for histidine, 0.013 and 0.027 for phenylalanine, and 0.04 and 0.08 for tryptophan.

15. The process of claim 1, wherein the harvesting of EPO is performed at a time between day 9 and day 15 of the fed-batch process.

16. The process of claim 15, wherein the harvesting takes place at day 12 of the fed-batch process.

17. The process of claim 1, further comprising:
   d) separation of undesired components from the produced EPO molecules to obtain EPO with an average sialic acid content per EPO molecule of at least 12.

18. The process of claim 17, wherein EPO is obtained with an average sialic acid content per EPO molecule of between 12 and 15.

19. A process for recombinant production of erythropoietin (EPO) at a concentration of at least 5000 eU/ml, the process comprising:
   a) providing a human embryonic retina cell that expresses at least an adenoviral E1A protein, and said cell further comprising nucleic acid encoding EPO under control of a heterologous promoter;
   b) culturing the cell in a culture medium in a fed-batch process, wherein at least once during said culturing according to needs of nutrients at least one essential amino acid and at least one carbohydrate are added depending on the requirements of the cells, adding, in an end concentration in mmoles/l of freshly added component per 10×10⁶ cells/ml, between 4.0 and 8.0 for glucose, and between 1.17 and 3.47 for glutamine; and
   c) harvesting EPO from the culture medium, wherein the EPO is present at a concentration of at least 5000 eU/ml.

* * * * *

UNITED STATES PATENT AND TRADEMARK OFFICE
CERTIFICATE OF CORRECTION

PATENT NO. : 7,608,431 B2  Page 1 of 1
APPLICATION NO. : 11/331861
DATED : October 27, 2009
INVENTOR(S) : Christopher A. Yallop It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 409 days.

Signed and Sealed this

Twelfth Day of October, 2010

David J. Kappos
*Director of the United States Patent and Trademark Office*